US008349899B1

(12) United States Patent
Arterburn et al.

(10) Patent No.: US 8,349,899 B1
(45) Date of Patent: Jan. 8, 2013

(54) SELECTIVE INHIBITORS OF EG5 MOTORS AND METHODS OF USE

(75) Inventors: Jeffrey Arterburn, Las Cruces, NM (US); Charles Shuster, Las Cruces, NM (US)

(73) Assignee: Arrowhead Center, Inc., Las Cruces, NM (US)

( * ) Notice: Subject to any disclaimer, the term of this patent is extended or adjusted under 35 U.S.C. 154(b) by 327 days.

(21) Appl. No.: 12/630,769

(22) Filed: Dec. 3, 2009

Related U.S. Application Data

(60) Provisional application No. 61/119,663, filed on Dec. 3, 2008.

(51) Int. Cl.
*A61K 31/135* (2006.01)
*C07C 217/54* (2006.01)
(52) U.S. Cl. .................................. 514/648; 564/317
(58) Field of Classification Search ........................ None
See application file for complete search history.

(56) References Cited

U.S. PATENT DOCUMENTS

| | | | |
|---|---|---|---|
| 3,531,490 A | 9/1970 | Friedman et al. |
| 3,624,143 A | 11/1971 | Shen et al. |
| 3,629,452 A | 12/1971 | Kalopissis et al. |
| 3,634,365 A | 1/1972 | Roberts et al. |
| 3,950,387 A | 4/1976 | Joullie et al. |
| 4,071,405 A | 1/1978 | Soda et al. |
| 4,248,890 A | 2/1981 | Maffrand |
| 5,399,363 A | 3/1995 | Liversidge et al. |
| 5,466,468 A | 11/1995 | Schneider et al. |
| 5,543,158 A | 8/1996 | Gref et al. |
| 5,580,579 A | 12/1996 | Ruddy et al. |
| 5,629,001 A | 5/1997 | Michael et al. |
| 5,641,515 A | 6/1997 | Ramtoola |
| 5,725,871 A | 3/1998 | Illum |
| 5,756,353 A | 5/1998 | Debs |
| 5,780,045 A | 7/1998 | McQuinn et al. |
| 5,792,451 A | 8/1998 | Sarubbi et al. |
| 5,804,212 A | 9/1998 | Illum |
| 5,861,529 A | 1/1999 | Baudoin et al. |
| 6,166,072 A | 12/2000 | Bell et al. |
| 6,229,041 B1 | 5/2001 | Brown et al. |
| 6,613,308 B2 | 9/2003 | Bartus et al. |
| 6,677,459 B2 | 1/2004 | Gabriel et al. |
| 6,696,456 B1 | 2/2004 | Pikul et al. |
| 6,730,784 B2 | 5/2004 | Mita et al. |
| 6,765,109 B1 | 7/2004 | Brown et al. |
| 7,011,960 B2 | 3/2006 | Bleicher et al. |
| 7,115,769 B2 | 10/2006 | Gimi et al. |
| 7,192,945 B2 | 3/2007 | Starke et al. |
| 7,358,248 B2 | 4/2008 | Whitehouse et al. |
| 7,498,356 B2 | 3/2009 | Whitehouse et al. |
| 7,504,512 B2 | 3/2009 | Augeri et al. |
| 7,531,162 B2 | 5/2009 | Collins et al. |
| 2006/0281926 A1 | 12/2006 | Gimi et al. |
| 2009/0137473 A1 | 5/2009 | Martin et al. |
| 2009/0239922 A1 | 9/2009 | Abrams et al. |

FOREIGN PATENT DOCUMENTS

| | | | |
|---|---|---|---|
| EP | 1308457 | * | 8/2002 |
| WO | WO-2008/114505 A1 | | 9/2008 |
| WO | WO-2009/067800 A1 | | 6/2009 |

OTHER PUBLICATIONS

Ambrose, J. C. et al., "A Minus-End-directed Kinesin with Plus-End Tracking Protein Activity Is Involved in Spindle Morphogenesis", Molecular Biology of the Cell, vol. 16, The American Society for Cell Biology, Apr. 2005, 1584-1592.
Beer, Tomas M. et al., "Southwest Oncology Group Phase II Study of Ispinesib in Androgen-Independent Prostate Cancer Previously Treated with Taxanes", Clinical Genitourinary Cancer, vol. 6, No. 2, Sep. 2008, 103-109.
Bergnes, Gustave et al., "Mitotic Kinesins: Prospects for Antimitotic Drug Discovery", Current Topics in Medicinal Chemistry, vol. 5, Bentham Science Publishers Ltd., 2005, 127-145.
Blangy, Anne et al., "Phsphorylation by p34cdc2 Regulates Spindle Association of Human Eg5, a Kinesin-Related Motor Essential for Bipolar Spindle Formation In Vivo", Cell, vol. 83, Cell Press, Dec. 29, 1995, 1159-1169.
Brier, Sebastien et al., "Identification of the Protein Binding Region of S-Trityl-L-Cysteine, a New Potent Inhibitor of the Mitotic Kinesin Eg5", Biochemistry, vol. 43, No. 41, American Chemical Society, 2004, 13072-13082.
Brier, Sebastien et al., "Molecular Dissection of the Inhibitor Binding Pocket of Mitotic Kinesin Eg5 Reveals Mutants that Confer Resistance to Antimitotic Agents", J. Mol. Biol., vol. 360, Elsevier Ltd., 2006, 360-376.
Brier, Sebastien et al., "Use of hydrogen/deuterium exchange mass spectrometry and mutagenesis as a tool to identify the binding region of inhibitors targeting the human mitotic kinesin Eg5", Rapid Communications in Mass Spectrometry, vol. 20, John Wiley & Sons, Ltd., 2006, 456-462.
Chahal, Francina et al., "Novel Cancer-Associated Antibody and Antigen", U.S. Appl. No. 60/990,494, filed Nov. 27, 2007.
Cochran, Jared C. et al., "ATPase Mechanism of Eg5 in the Absence of Microtubules: Insight into Microtubule Activation and Allosteric Inhibition by Monastrol", Biochemistry, vol. 44, No. 50, Dec. 20, 2005, 16633-16648.
Debonis, Salvatore et al., "In vitro screening for inhibitors of the human mitotic kinesin Eg5 with antimitotic and antitumor activities", Molecular Cancer Therapeutics, vol. 3, No. 9, Apr. 9, 2004, 1079-1090.
Debonis, Salvatore et al., "Structure-Activity Relationship of S-Trityl-L-Cysteine Analogues as Inhibitors of the Human Mitotic Kinesin Eg5", Journal of Medicinal Chemistry, vol. 51, No. 5, American Chemical Society, 2008, 1115-1125.

(Continued)

*Primary Examiner* — Joseph K. McKane
*Assistant Examiner* — Alicia L Otton
(74) *Attorney, Agent, or Firm* — Samantha A. Updegraff; Janeen Vilven; Peacock Myers, P.C.

(57) ABSTRACT

Embodiments of the present invention comprises a compound of formula I or its enantiomer, diastereomer, stereoisomer or its pharmaceutically acceptable salt, methods of use and methods of synthesis.

Formula I

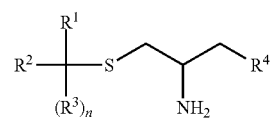

17 Claims, 1 Drawing Sheet

OTHER PUBLICATIONS

Duhl, David M. et al., "Inhibitors of kinesin motor proteins—research and clinical progress", Current Opinion in Drug Discovery & Development, vol. 8, No. 4, The Thomson Corporation, 2005, 431-436.

Funk, C. J. et al., "Development of high-throughput screens for discovery of kinesin adenosine triphosphatase modulators", Analytical Biochemistry, vol. 329, Elsevier Inc., 2004, 68-76.

Gennaro, ED., Alfonso R., "Remington's Pharmaceutical Sciences", Mack Publishing Company, Easton, Pennsylvania, 1990, 1289-1329.

George, Olivia et al., "Bisphenol a Directly Targets Tubulin to Disrupt Spindle Organization in Embryonic and Somatic Cells", ACS Chemical Biology, vol. 3, No. 3, 2008, 167-179.

Gorbsky, Gary J., "Mitosis: MCAK under the Aura of Aurora B", Current Biology, vol. 14, Elsevier Ltd., May 4, 2004, R346-R348.

Goshima, Gohta et al., "The roles of microtubule-based motor proteins in mitosis: comprehensive RNAi analysis in the *Drosophila* S2 cell line", The Journal of Cell Biology, vol. 162, No. 6, The Rockefeller University Press, Sep. 15, 2003, 1003-1016.

Neumann, E. et al., "Human Inetochore-associated Kinesin CENP-E Visualized at 17 A Resolution Bound to Microtubules", J. Mol. Biol., vol. 362, Elsevier Ltd., 2006, 203-211.

Ogo, Naohisa et al., "Synthesis and biological evaluation of L-cysteine derivatives as mitotic kinesin Eg5 inhibitors", Bioorganic & Medicinal Chemistry Letters, vol. 17, Elsevier Ltd., 2007, 3921-3924.

Palchhaudhuri, Rahul et al., "The Complex Role of the Triphenylmethyl Motif in Anticancer Compounds", J. Am. Chem. Soc., vol. 130, American Chemical Society, 2008, 1 0274-10281.

Petra, Danielle G. et al., "Aminosulf(ox)ides as Ligands for Iridium(I)-Catalyzed Asymmetric Transfer Hydrogenation", J. Org. Chem., vol. 65, American Chemical Society, 2000, 3010-3017.

Schmidt, Mathias et al., "Mitotic drug targets and the development of novel anti-mitotic anticancer drugs", Drug Resistance Updates, vol. 10, Elsevier Ltd., 2007, 162-181.

Skoufias, Dimitrios A. et al., "S-Trityl-L-cysteine is a Reversible, Tight Binding Inhibitor of the Human Kinesin Eg5 That Specfically Blocks Mitotic Progression", The Journal of Biological Chemistry, vol. 281, No. 26, The American Society for Biochemistry and Molecular Biology, Inc., Jun. 30, 2006, 17559-17569.

Sudakin, Valery et al., "Targeting Mitosis for Anti-Cancer Therapy", Biodrugs, vol. 21, No. 4, Adis Data Information BV, 2007, 225-233.

Turner, Jennifer et al., "Crystal Structure of the Mitotic Spindle Kinesin Eg5 Reveals a Novel Conformation of the Neck-linker", The Journal of Biological Chemistry, vol. 276, No. 27, The American Society for Biochemistry and Molecular Biology, Inc., 2001, 25496-25502.

Weisburger, E. K. et al., "Fluorenylcysteines", Notes, Journal of the Chemical Society, Jan. 1, 1964, 515-518.

Zee-Cheng, Kwang Y. et al., "Structural Modification of S-Trityl-L-cysteine. Preparation of Some S-(Substituted Trityl)-L-cysteines and Dipeptides of S-Trityl-L-cysteine", Journal of Medicinal Chemistry, vol. 15, No. 1, 1972, 13-16.

Zee-Cheng, Kwang-Yuen et al., "Experimental Antileukemic Agents. Preparation and Structure-Activity Study of S-tritylcysteine and Related Compounds", Journal of Medicinal Chemistry, vol. 13, No. 3, 1970, 414-418.

Zhang, Yingjie et al., "Progress on Kinesin Spindle Protein Inhibitors as Anti-Cancer Agents", Anti-Cancer Agents in Medicinal Chemistry, vol. 8, Bentham Science Publishers Ltd., 2008, 698-704.

Zheng, Yan et al, "A Magnetic Biomimetic Nanocatalyst for Cleaving Phosphoester and Carboxylic Ester Bonds under Mild Conditions", Organic Letters, vol. 8, No. 15, American Chemical Society, Jun. 27, 2006, 3215-3217.

Zhou, Jun et al., "Targeting Microtubules for Cancer Chemotherapy", Curr. Med. Chem—Anti-Cancer Agents, vol. 5, Bentham Science Publishers Ltd., 2005, 65-71.

Haque, Saad A. et al., "Monastrol, a Prototype Anti-Cancer Drug That Inhibits a Mitotic Kinesin, Induces Rapid Bursts of Axonal Outgrowth From Cultured Postmitotic Neurons", Cell Motility and the Cytoskeleton, vol. 28, Wiley-Liss, Inc., 2004, 10-16.

Hotha, Srinivas et al., "HR22C16: A Potent Small-Molecule Probe for the Dynamics of Cell Division", Angew. Chem. Int. Ed., vol. 42, Wiley-VCH Verlag GmbH & Co. KGaA, Weinheim, 2003, 2379-2382.

Jordan, Mary A. et al., "Microtubules as a Target for Anticancer Drugs", Nature Reviews, vol. 4, Apr. 2004, 253-265.

Kapoor, Tarun M. et al., "Probing Spindle Assembly Mechanisms with Monastrol, a Small Molecule Inhibitor of the Mitotic Kinesin, Eg5", The Journal of Cell Biology, vol. 150, The Rockefeller University Press, Sep. 4, 2000, 975-988.

Kessel, David et al., "Effects of S-(Trityl)-L-Cysteine and Its Analogs on Cell Surface Properties of Leukeumia L1210 Cells", Biochemical Pharmacology, vol. 25, Pergamon Press, Great Britain, 1976, 1893-1897.

Klein, Emmanuel et al., "New chemical tools for investigatin human mitotic kinesin Eg5", Bioorganic & Medicinal Chemistry, vol. 15, Elsevier Ltd., 2007, 6474-6488.

Lad, Latesh et al., "Mechanism of Inhibition of Human KSP by Ispinesib", Biochemistry, vol. 47, No. 11, American Chemical Society, 2008, 3576-3585.

Lawrence, Carolyn J. et al., "A standardized kinesin nomenclature", JCB, vol. 167, No. 1, The Rockefeller University Press, Oct. 11, 2004, 19-22.

Lee, Christopher W. et al., "A phase II study of ispinesib (SB-715992) in patients with mestastatic or recurrent malignant melanoma: a National Cancer Institute Canada Clinical Trials Group trial", Invest New Drugs, vol. 26, Springer, 2008, 249-255.

Luo, Lusong et al., "ATP-competitive inhibitors of the mitotic kinesin KSP that function via an allosteric mechanism", Nature Chemical Biology, vol. 3, No. 11, Nov. 2007, 722-726.

Maliga, Zoltan et al., "A Pathway of Structural Changes Produced by Monastrol Binding to Eg5", The Journal of Biological Chemistry, vol. 281, No. 12, The American Society for Biochemistry and Molecular Biology, Inc., Mar. 24, 2006, 7977-7982.

Maliga, Zoltan et al., "Evidence that Monastrol Is an Allosteric Inhibitor of the Mitotic Kinesin Eg5", Chemistry & Biology, vol. 9, Elsevier Science Ltd., Sep. 2002, 989-996.

Maliga, Zoltan et al., "Small-molecule and mutational analysis of allosteric Eg5 in inhibition by monastrol", BMC Chemical Biology, vol. 6, No. 2, Feb. 27, 2006, 1-9.

Mao, Yinghui et al., "Microtubule capture by CENP-E silences BubR1-dependent mitotic checkpoint signaling", The Journal of Cell Biology, vol. 170, No. 6, The Rockefeller University Press, Sep. 12, 2005, 873-880.

Mayer, Thomas U. et al., "Small Molecule Inhibitor of Mitotic Spindle Bipolarity Idenitifed in a Phenotype-Based Screen", Science, vol. 286, Oct. 29, 1999, 971-974.

Mazumder, Manjari et al., "Chromokinesins: multitalented players in mitosis", Trends in Cell Biology, vol. 15, No. 7, Elsevier Ltd., Jul. 2005, 349-355.

Moore, Ayana T. et al., "MCAK associates with the tips of polymerizing microtubules", The Journal of Cell Biology, vol. 169, No. 3, The Rockefeller University Press, May 9, 2005, 391-397.

Mountain, Vicki et al., "The Kinesin-related Protein, HSET, Opposes the Activity of Eg5 and Cross-links Microtubules in the Mammalina Mitotic Spindle", The Journal of Cell Biology, vol. 147, No. 2, The Rockefeller University Press, Oct. 18, 1999, 351-365.

Murray, Andrew W., "Cell Cycle Extracts", Methods in Cell Biology, vol. 36, Academic Press, Inc., 1991, 581-605.

\* cited by examiner

SELECTIVE INHIBITORS OF EG5 MOTORS AND METHODS OF USE

CROSS-REFERENCE TO RELATED APPLICATIONS

This application claims priority to and the benefit of the filing of U.S. Provisional Patent Application Ser. No. 61/119,663, entitled "Selective Inhibitors of Eg5 Motors as Potential Anti-Cancer Chemotherapeutics", filed on Dec. 3, 2008, and the specification thereof is incorporated herein by reference.

BACKGROUND

Approximately 1.4 million Americans are diagnosed with cancer each year. In addition, approximately 550,000 Americans die from cancer each year in the United States alone. Prostate and lung cancers are the leading causes of death in men while breast and lung cancer are the leading causes of death in women.

Cellular differentiation, growth, function and death are regulated by a complex network of mechanisms at the molecular level in a multicellular organism. In the healthy animal or human, these mechanisms allow the cell to carry out its designed function and then die at a programmed rate.

Abnormal cellular proliferation, notably hyperproliferation, can occur as a result of a wide variety of factors, including genetic mutation, infection, exposure to toxins, autoimmune disorders, and benign or malignant tumor induction.

A tumor, also called a neoplasm, is a new growth of tissue in which the multiplication of cells is uncontrolled and progressive. A benign tumor is one that lacks the properties of invasion and metastasis and is usually surrounded by a fibrous capsule. A malignant tumor (i.e., cancer) is one that is capable of both invasion and metastasis. Malignant tumors also show a greater degree of anaplasia (i.e., loss of differentiation of cells and of their orientation to one another and to their axial framework) than benign tumors.

Proliferative disorders are currently treated by a variety of classes of compounds including alkylating agents, antimetabolites, natural products, enzymes, biological response modifiers, miscellaneous agents, hormones and antagonists.

Natural and synthetic small molecules that target the microtubule cytoskeleton have proven invaluable in understanding the mechanisms of cell division. Modulators of the microtubule polymerization (such as colcimid and paciltaxel) interfere with cell division by altering microtubule dynamics, resulting in extended mitotic arrest and cell death (Jordan and Wilson, 2004; Zhou and Giannakakou, 2005). Microtubule disrupters have found use as chemotherapeutics, but because microtubules are essential for many cellular functions, toxicity issues limit their use as anti-cancer agents. Kinesins may be potential targets for anti-proliferative drugs (Bergnes et al., 2005; Duhl and Renhowe, 2005). Kinesins are motor proteins associated with microtubules. There are roughly 14 different kinesins (Lawrence et al., 2004), whose functions range from vesicular transport to cell division. RNAi analysis of 25 *Drosophila* kinesins revealed that four members were involved in mitotic spindle assembly (Goshima and Vale, 2003). One of these is the class five kinesin spindle protein (KSP) and is referred to in the literature as Kinesin 5, KSP or Eg5. Eg5 is a plus-end directed motor separates the spindle poles early in mitosis (Blangy et al., 1995). Eg5 is antagonized by minus-end directed kinesin known as HSET or NCD (Mountain et al., 1999), and inhibition of Eg5 results in spindle collapse and formation of a monopolar spindle. Because chromosomes are unable to form normal bipolar attachments to the spindle, the cell arrests in mitosis, and eventually dies by apoptosis (Skoufias et al., 2006). Although there are reports that Eg5 plays a role in neuronal development (Hague et al., 2004), there are no other known functions outside of mitosis in adults, and disruption of Eg5 has no effect on interphase microtubule dynamics or organization (Mayer et al., 1999b; Hotha et al., 2003; DeBonis et al., 2004).

Several Eg5 inhibitors, including monastrol (Mayer et al., 1999a), S-trityl-L-cysteine (2.5) (STLC) (Mayer et al., 1999b; Hotha et al., 2003; DeBonis et al., 2004) and more recently Ispinesib (Luo et al., 2007) have been identified. All act as specific, allosteric inhibitors of Eg5 ATPase activity (Brier et al., 2004; Brier et al., 2006a; Skoufias et al., 2006), and exhibit no inhibitory activity against the other kinesin family members (Mayer et al., 1999b; Skoufias et al., 2006). All three molecules bind an allosteric site in between a helix 3 and Loop 5 domain of the Eg5 motor domains (Turner et al., 2001; Maliga et al., 2002; Brier et al., 2004; Brier et al., 2006a; Brier et al., 2006b; Maliga and Mitchison, 2006; Maliga et al., 2006), and it has been proposed that the longer Loop 5 domain found in Eg5 class 5 kinesins explains in part the specificity of these drugs to class 5 kinesins (Turner et al., 2001). And while the kinetics of inhibition are different between these molecules, all appear to act through a similar mechanism where ADP release is perturbed without blocking motor domain release from the microtubule (Cochran and Gilbert, 2005; Skoufias et al., 2006; Lad et al., 2008). All three inhibitors have demonstrated the ability to kill cancer cells (Mayer et at., 1999b; Skoufias et al., 2006; Luo et al., 2007), and while monastrol is not effective at pharmacologically relevant concentrations, Ispinesib is currently in phase II clinical trials as a treatment directed to a number of malignancies (Beer et al., 2008; Lee et al., 2008) (check reviews for additional citations).

STLC is a derivative of the amino acid cysteine, with a trityl group linked to the sulfur on the cysteine side chain. STLC has almost a hundred fold lower $IC_{50}$ than monastrol in vitro and in vivo (DeBonis et al., 2004; Skoufias et al., 2006), and cells exposed to STLC undergo a reversible mitotic arrest that lasts up to 72 hours before cells undergo apoptosis (DeBonis et al., 2004; Brier et al., 2006a). Eg5 mutants that confer monastrol resistance also confer resistance to STLC, lending further support to the notion that STLC binds the same allosteric site as monastrol (Brier et al., 2006a; Maliga and Mitchison, 2006). The cell permeability of STLC is facilitated by the non-polar trityl group, since the carboxylic acid and amine groups are charged to form a zwitterionic species at physiological pH. Thus, while the non-polar trityl group greatly increases cell permeability, the charged groups are likely accounting for the relatively high $IC_{50}$ for STLC. Moreover, compound 2.5 (STLC) as well as the other Eg5 inhibitors appear to be specific to vertebrate Eg 5 isoforms, thus limiting its use in nonmammalian model systems.

S-Trityl-L-cysteine (STLC) is a known inhibitor of Eg5. (Zee-Cheng et al. Experimental antileukemic agents: Preparation and structure-activity study of S-tritylcysteine and related compounds. J. Med. Chem. (1970), 13(3), 414-18; Zee-Cheng, et al. Structural modification of S-trityl-L-cysteine. Preparation of some S-(substituted trityl)-L-cysteines and dipeptides of S-trityl-L-cysteine. J. Med. Chem. (1972), 15(1), 13-16; David Kessel, et al. Effects of S-(trityl)-L-cysteine and its analogs on cell surface properties of leukemia L1210 cells. Biochemical Pharmacology (1976), 25(16), 1893-7; Sebastien Brier, et al. Molecular Dissection of the Inhibitor Binding Pocket of Mitotic Kinesin Eg5 Reveals Mutants that Confer Resistance to Antimitotic Agents. Journal of Molecular Biology (2006), 360(2), 360-376. Naohisa Ogo, et al. (2007). Synthesis and biological evaluation of L-cysteine derivatives as mitotic kinesin Eq5 inhibitors. Bioorg. Med. Chem. Lett. (2007) 17, 3921-3924; Emmanuel Klein, et al. New chemical tools for investigating human mitotic kinesin Eg5. (2007) Bioorg. Med. Chem. Lett. (2007), 17, 6474-6488; and Salvatore DeBonis, et al. Structure-Activity Relationship of S-Trityl-L-Cysteine Analogues as Inhibitors of the Human Mitotic Kinesin Eq5. J. Med. Chem. (2008), 51(5), 1115-1125. Closely related derivatives have been proposed as agents for the treatment of cell proliferative disease. (Akira Asai, et al. Eq5 inhibitor and agent for treatment of cell proliferative disease containing the same. PCT Int. Appl. (2008), 34 pp. CODEN: PIXXD2 WO 2008114505 A1 20080925 CAN 149:370564 AN 2008:1157799 CAPLUS).

BRIEF SUMMARY OF EMBODIMENTS OF THE PRESENT INVENTION

One embodiment of the present invention comprises a compound of formula I or its enantiomer, diastereomer, stereoisomer or its pharmaceutically acceptable salt,

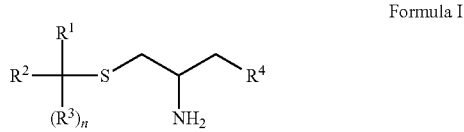

Formula I wherein $R^1$ is independently selected from a substituted or unsubstituted alkyl group, a substituted or an unsubstituted alkenyl group, a substituted or an unsubstituted alkynyl group, a substituted or an unsubstituted cyloalkyl group, a substituted or an unsubstituted cycloalkenyl group, a substituted or an unsubstituted aryl group, a substituted or an unsubstituted heterocyclic group or a substituted or an unsubstituted heteroaryl group; $R^2$ is independently selected from the substituted or the unsubstituted alkyl group, the substituted or the unsubstituted alkenyl group, the substituted or the unsubstituted alkynyl group, the substituted or the unsubstituted cyloalkyl group, the substituted or the unsubstituted cycloalkenyl group, the substituted or the unsubstituted aryl group, the substituted or the unsubstituted heterocyclic group or the substituted or the unsubstituted heteroaryl group wherein $R^2$ may be the same or different with respect to R' and/or $R^3$, $(R^3)_n$, wherein n is 0 or 1; and when n is 1, $R^3$ is independently selected from the substituted or the unsubstituted alkyl group, the substituted or the unsubstituted alkenyl group, the substituted or the unsubstituted alkynyl group, the substituted or the unsubstituted cyloalkyl group, the substituted or the unsubstituted cycloalkenyl group, the substituted or the unsubstituted aryl group, the substituted or the unsubstituted heterocyclic group or the substituted or the unsubstituted heteroaryl group wherein $R^3$ may be the same or different with respect to R' and/or $R^2$, and $R^4$ is independently selected from a hydroxy group, an alkoxy group, an amino or a substituted amino group, a halide group, the substituted or the unsubstituted alkyl group, the substituted or the unsubstituted alkenyl group, the substituted or the unsubstituted alkynyl group, the substituted or the unsubstituted cyloalkyl group, the substituted or the unsubstituted cycloalkenyl group, the substituted or the unsubstituted aryl group, the substituted or the unsubstituted heterocyclic group or the substituted or the unsubstituted heteroaryl group.

$R^4$ can be covalently bonded to $R^3$ when n is 1, or when n is 0, $R^4$ is covalently bonded to the di-substituted methyl carbon bonded to $R^1$ and $R^2$.

The compound of formula I can also be selected from a group consisting of compounds 1.0, 1.2, 1.3, 1.4, 1.5, 1.6, 1.7, 1.8, 1.9, 2.0, 2.1, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, and 6.4.

The compound of formula I can optionally comprise a therapeutic agent.

Another embodiment of the present invention preferably comprises a pharmaceutical composition which comprises a compound of formula I, or a pharmaceutically acceptable salt, solvate, solvate of such a salt, or an in vivo hydrolysable ester formed on an available carboxy or hydroxyl thereof, or an in vivo hydrolysable amide formed on an available carboxy thereof as disclosed above, in association with a pharmaceutically-acceptable diluent or carrier.

A further embodiment of the present invention comprises a process for preparing a compound of the formula I which includes reducing 2-amino-3-mercaptopropanoic acid or a derivative thereof comprising the steps of: using excess borane reagent in an organic solvent; using an inert atmosphere; and quenching excess borane reagent with a second reagent. The second reagent of this embodiment preferably comprises dimethylformamide.

One embodiment of the present invention comprises a method of inhibiting cell activity. This method preferably includes providing a compound of formula I to the cell to inhibit the cell activity. The cell activity can be activity of Eg5 or an Eg5 ortholog and/or activity of isolated Eg5 and/or chromosome movement and/or spindle pole separation and/or establishment of spindle bipolarity and/or mitosis of a dividing cell. In this embodiment, measurement of the cell activity after contact with formula I is preferably performed. In one embodiment, rate of mitosis of a dividing cell is measured after contacting formula I with a cell.

Another embodiment of the present invention comprises a method of treating a proliferative disease in a patient in need thereof. This embodiment preferably comprises administering to a patient in need thereof a pharmaceutically acceptable amount of a compound of formula I or a salt with organic or inorganic acid to treat a proliferative disease. This embodiment can further comprise monitoring the proliferative disease in the patient after administration of a pharmaceutically acceptable amount of the compound. The compound is preferably administered in a therapeutically effective dose by intravenous drug route or by oral route. The proliferative disease can be cancer and the cancer patient can be monitored for cancer progression.

Aspects and further scope of applicability of the present invention will be set forth in part in the detailed description to follow, taken in conjunction with the accompanying drawings, and in part will become apparent to those skilled in the art upon examination of the following, or may be learned by practice of the invention. The aspects of embodiments of the present invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Definitions

Figure 1:
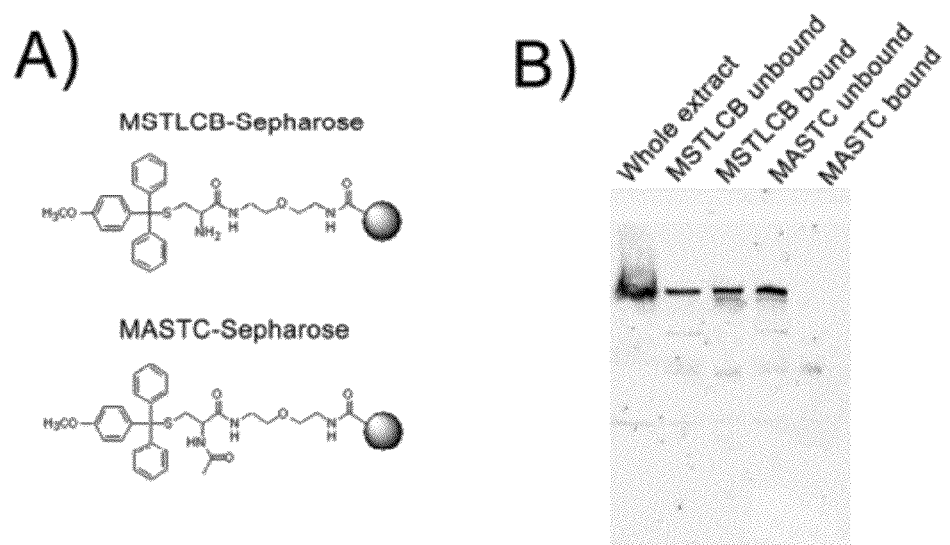
FIG. 1A is a structure of compound 7.6 (MSTLCB-Sepharose) and compound 7.7 (MASTC-Sepharose) affinity probes.
FIG. 1B is a Western blot of cell extracts affinity-fractionated over the compounds shown in FIG. 1A, probed for the presence of Eg5.

As used herein "a" means one or more.

As used herein "aryl" or "aryl group" refers to a totally unsaturated, mono- or bi-cyclic carbon ring that contains 3-14 atoms. Preferably "aryl" is a single ring (e.g., phenyl) or multiple condensed rings (e.g., naphthyl or anthryl), wherein condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

As used herein "substituted aryl" refers to aryl groups which are substituted with one or more, preferably from 1 to 3 substituents, and more preferably 1 to 2 substituents. Suitable substituents include halides, hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, carboxyl, carboxyl esters, cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, amino sulfonyl ($NH_2$—$SO_2$—), and substituted amino sulfonyl.

As used herein "heterocyclic" or "heterocyclic group" refers to a saturated, partially unsaturated or unsaturated group having a single ring or multiple condensed rings, including fused bridged and spiro ring systems, from 3 to 10 ring atoms including from 1 to 4 hetero atoms selected from the group consisting of nitrogen, sulfur and oxygen as ring members; in fused ring systems, one or more of the rings can be cycloalkyl, aryl or heteroaryl provided that the point of attachment is through the heterocyclic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with one or more and preferably from 1 to 3 substituents, selected from the substituents described herein. Suitable substituents include those described herein for alkyl and cycloalkyl groups.

As used herein "alkoxy" or "alkoxy group" refers to the group "alkyl-O—" which includes, by way of example, methoxy, ethoxy, n-propoxy, iso-propoxy, n-butoxy, t-butoxy, sec-butoxy, n-pentoxy and the like, wherein alkyl is defined herein.

As used herein "substituted alkoxy" refers to the group "substituted alkyl-O—" groups which are substituted with one or more, preferably from 1 to 3 substituents, and more preferably 1 to 2 substituents. Suitable substituents include halides, hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, carboxyl, carboxyl esters, cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, amino sulfonyl ($NH_2$—$SO_2$—), and substituted amino sulfonyl.

As used herein "amino", "amine", "amino group", or "amine group" refer to the group —$NH_2$ or $NH_3^+$ at physiologic pH.

As used herein "substituted amino" refers to the group—NR'R" where R' and R" are independently selected from the group consisting of hydrogen, when R' or R" is another substituent; alkyl, substituted alkyl, alkenyl, substituted alkenyl, alkynyl, substituted alkynyl, aryl, substituted aryl, cycloalkyl, substituted cycloalkyl, halides, heteroaryl, substituted heteroaryl, heterocyclic, substituted heterocyclic, —$SO_2$-alkyl, —$SO_2$-substituted alkyl, and where R' and R" are optionally joined, together with the nitrogen bound thereto, to form a heterocyclic or substituted heterocyclic group; provided that R' and R" are not both hydrogen. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" is hydrogen.

As used herein "alkyl" refers to monovalent saturated aliphatic straight chain, branched, fused ring system or cyclic hydrocarbyl groups having from 1 to 10 carbon atoms and more preferably 1 to 4 carbon atoms. This term is exemplified by groups such as methyl, ethyl, n-propyl, iso-propyl, iso-butyl, n-butyl, t-butyl, n-pentyl, and the like. The term "linear alkyl" refers to an alkyl group that is not branched. "Substituted alkyl" refers to an alkyl group having one or more substituents, including branched substituents, frequently from 1 to 4, and preferably 1 to 2, substituents. Suitable substituents for alkyl groups are selected from the group consisting of substituted or unsubstituted alkoxy, substituted or unsubstituted acyl, substituted or unsubstituted acylamino, substituted or unsubstituted acyloxy, substituted or unsubstituted amino, substituted or unsubstituted aminoacyl, aryl, substituted aryl, aryloxy, substituted aryloxy, cyano, halides, hydroxyl, nitro, carboxyl, oxo, hydroxy-imino, substituted or unsubstituted alkoxy-imino carboxyl C1-C4 esters, cycloalkyl, substituted cycloalkyl, substituted or unsubstituted spirocycloalkyl, heteroaryl, substituted heteroaryl, heterocyclic, substituted heterocyclic, $SO_2$-alkyl, —$SO_2$-substituted alkyl wherein said substituents are defined herein. Preferred substituents for alkyl groups include alkoxy, hydroxy, halo or halide which is preferably F, Cl, Br, or I, cyano, oxo, substituted or unsubstituted amino, substituted or unsubstituted acyloxy and substituted or unsubstituted acylamino.

As used herein "cycloalkyl" refers to cyclic hydrocarbyl groups or fused ring systems having from 1 to 10 carbon atoms and more preferably 5 to 7 carbon atoms. This term is exemplified but not limited to groups such as cyclopropyl, cyclobutyl, cyclopentyl, cyclohexyl, cycloheptyl and the like.

As used herein "substituted cycloalkyl" refers to cyclic hydrocarbyl groups or fused ring systems that are substituted with from 1 to 3 substituents, preferably 1 or 2 substituents, selected from the same group of substituents defined for substituted aryl.

As used herein "alkylamino" refers to an alkyl group (typically one to ten carbon atoms) wherein from one or more of the $C_1$-$C_{10}$ alkyl group's hydrogen atoms is replaced with an amine or a substituted amine of formula —N(R')$_2$, wherein each occurrence of R' is independently —H or ($C_1$-$C_{10}$)alkyl. Examples of aminoalkyl groups include, but are not limited to, —CH$_2$ NH$_2$, —CH$_2$CH$_2$NH$_2$—, —CH$_2$CH$_2$CH$_2$NH$_2$, —CH$_2$CH$_2$CH$_2$CH$_2$NH$_2$, —CH$_2$CH$_2$CH$_2$CH$_2$CH$_2$NH$_2$, —CH$_2$CH$_2$CH$_2$CH$_2$CH$_2$CH$_2$NH$_2$, —CH$_2$CH$_2$CH$_2$N(CH$_3$)$_2$, t-butylaminomethyl, isopropylaminomethyl and the like.

As used herein "halo", "halide", or "halogen" substituent group refers to F, Cl, Br, or I.

As used herein "arylamino" refers to an organic compound formed from an aromatic hydrocarbon that has at least one amino or substituted amino group joined to it.

As used herein "heteroaryl" or "heteroaryl group" refers to a totally unsaturated, single ring or multiple condensed rings containing 3 to 14 atoms of which at least one atom is chosen from nitrogen, sulphur or oxygen, which may, unless otherwise specified, be carbon or nitrogen linked. In one embodiment, the nitrogen and/or the sulfur ring atom(s) of the heteroaryl group are optionally oxidized to provide for the N-oxide (N→O) sulfinyl, or sulfonyl moieties.

"Substituted heteroaryl" refers to heteroaryl groups that are substituted with from 1 to 3 substituents, preferably 1 or 2 substituents, selected from the same group of substituents defined for substituted aryl.

As used herein "alkenyl" refers to a linear or branched chain, unsaturated hydrocarbon possessing a single or multiple double bonds and having from 2 to 12 carbon atoms. For example, $C_1$-$C_6$ alkenyl is meant to include, but is not limited to, ethenyl, propenyl, isopropenyl, butenyl, butadienyl, pentenyl, isopentenyl, hexenyl and hexadienyl. An alkenyl group can be unsubstituted or optionally substituted with one or more substituents defined for substituted aryl.

As used herein "cyloalkenyl" refers to an unsaturated carbon ring possessing a single or multiple double bonds having from 3 to 12 carbon atoms. For example, $C_3$-$C_6$ cycloalkenyl is meant to include, but is not limited to cylopropenyl, cylobutenyl, cylopentenyl, cylohexenyl and cylohexadienyl. A cyloalkenyl group can be unsubstituted or optionally substituted with one or more substituents defined for substituted aryl.

As used herein "alkynyl" refers to a linear or branched chain, unsaturated hydrocarbon possessing a triple bond and having from 2 to 12 carbon atoms. For example, $C_2$-$C_6$ alkynyl is meant to include, but is not limited to ethynyl, propynyl, butynyl, pentynyl, and hexynyl. An alkynyl group can be unsubstituted or optionally substituted with one or more substituents defined for substituted aryl.

As used herein "racemic" refers to a compound which contains equal molar amounts of both enantiomeric forms of the compound.

As used herein "scalemic" refers to any non-racemic mixture of both enantiomeric forms of a chiral compound.

As used herein "stereoisomer" refers to compounds whose molecules have the same number and kind of atoms and the same atomic arrangement but differ in their special relationship.

As used herein "enantiomer" refers to one of an isomeric pair of compounds whose molecular structures are non-superimposable mirror images.

As used herein "diastereomer" refers to one of a pair of stereoisomers which are not mirror images of each other.

As used herein "patient" includes an animal (e.g., cow, horse, sheep, pig, chicken, turkey, quail, cat, dog, mouse, rat, rabbit, guinea pig, sea urchin, insects, and worms,), in one embodiment a mammal such as a non-primate and a primate (e.g., monkey and human), and in another embodiment a human. In specific embodiments, the patient is a human infant, child, adolescent or adult.

As used herein "therapeutic agent" includes chemotherapy, radiation therapy, immunotherapy, gene therapy, hormonal therapy, surgery, anticancer agents, photo therapy.

As used herein "anticancer agents" or "agent for the treatment of cancer" or "cancer therapeutics" refers to agents that include, by way of example only, agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies; monoclonal antibodies conjugated with anticancer drugs, toxins, and/or radionuclides; biological response modifiers (e.g. interferons and interleukins, etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other agents are well within the purview of one of skill in the art.

As used herein "Eg5 inhibitor" is a compound that is capable of inhibiting any measurable activity of Eg5. Preferably, a Eg5 inhibitor has an IC50 of less than 100 micromolar, more preferably less than 10 micromolar, and frequently less than 1 micromolar gastrointestinal tract cells.

As used herein "proliferative disease" includes any disease or condition affecting a vertebrate that is characterized by excessive or undesirable proliferating cells. The "method of treating a proliferative disease", according to this invention, includes a method for treating (inhibiting) the abnormal growth of cells, including transformed cells, in a patient in need of such treatment (e.g., a mammal such as a human), by administering, concurrently or sequentially, an effective amount of a Eg5 inhibitor alone or in combination with an effective amount of a chemotherapeutic agent and/or radiation. Abnormal growth of cells means cell growth independent of normal regulatory mechanisms (e.g., loss of contact inhibition), including the abnormal growth of tumor cells or benign and malignant cells of other proliferative diseases.

As used herein "cancer" and "cancerous" refer to or describe the physiological condition in mammals that is typically characterized by unregulated cell growth.

As used herein "tumor," refers to all neoplastic cell growth and proliferation, whether malignant or benign, and all precancerous and cancerous cells and tissues. The term "solid tumor" refers to a cancer or carcinoma of body tissues other than blood, bone marrow, and lymphoid system. Examples of solid tumors may be, but are not limited to, lung carcinoma, breast carcinoma, ovarian carcinoma, skin carcinoma, colon carcinoma, urinary bladder carcinoma, liver carcinoma, gastric carcinoma, prostate cancer, pancreatic cancer, renal cell carcinoma, nasopharyngeal carcinoma, squamous cell carcinoma, thyroid papillary carcinoma, cervical carcinoma, small cell lung carcinoma, non-small cell lung carcinoma, head and neck squamous cell cancer and sarcomas.

As used herein, "hematological cancer" refers to a cancer of the blood, and includes leukemia and malignant lymphoproliferative disorders, among others. "Leukemia" refers to a cancer of the blood, in which too many white or red blood cells are made, thus crowding out the other parts that make up the blood, such as platelets and normal red blood cells. It is understood that cases of leukemia are classified as acute or chronic. Cancer cells in acute leukemias are blocked at an immature stage, yet they continue to multiply. Consequently, there is a large accumulation of non-functional immature cells and the concomitant loss of functional cells. Chronic leukemias progress more slowly, with cancer cells developing to full maturity. Furthermore, the white blood cells may be myelogenous or lymphoid. Thus, certain forms of leukemia may be, by way of example, acute lymphotic (or lymphoblastic) leukemia (ALL); acute myelogenic leukemia (AML); chronic lymphocytic leukemia (CLL); or chronic myelogenic leukemia (CML); and myelodysplastic syndrome. "Malignant lymphoproliferative disorders" may refer to a lymphoma, such as Hodgkin's lymphoma, and non-Hodgkin's lymphoma, or multiple myeloma among others.

Some tumors described herein can be resistant to various therapeutic agents. "Resistant" means that the cancer is not substantially affected by a therapeutic agent at its normal administration rates, or at rates that are tolerated by the patient. A major form of resistance against a variety of the antineoplastic agents involves the function of a group of membrane protein pumps that extrude these cytotoxic molecules. "Multi-drug resistant pumps" may refer to the superfamily of ATP Binding Cassette (ABC) proteins, present in organisms from bacteria to humans. ABC transporter pumps are located in the plasma membrane of the cells or in the membrane of different cellular organelles, and mediate the translocation of various molecules across these barriers. Most ABC pumps utilize the energy of ATP hydrolysis for this transport activity (active transporters), but some ABC pumps form specific membrane channels.

As used herein "carriers" include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers comprise buffers such as phosphate, citrate, succinate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, polyethylene glycol (PEG), and Pluronics. Administration "in combination with" one or more further therapeutic agents includes simultaneous (concurrent) and consecutive administration in any order. Preferably, the therapeutic agents to be combined in such methods are both present at therapeutically relevant levels simultaneously in the body of the treated subject.

As used herein "treatment" refers to the application or administration of a Eg5 inhibitor to a subject, or application or administration of a Eg5 inhibitor to an isolated tissue or cell line from a subject, where the subject has a solid tumor or hematological cancer, a symptom associated with a solid tumor or hematological cancer, or a predisposition toward development of a solid tumor or hematological cancer, where the purpose is to cure, heal, alleviate, relieve, alter, remedy, ameliorate, improve, or affect the solid tumor or hematological cancer, any associated symptoms of the solid tumor or hematological cancer, or the predisposition toward development of the solid tumor or hematological cancer. The subject may be a mammal, and in some embodiments the subject is a human. Frequently, the subject is a human who has been diagnosed with at least one of the conditions described herein as suitable for treatment with the compounds and methods of the invention. In other embodiments a subject is a slime mold, fungi or plant of a cell derived therefrom.

By "treatment" is also intended the application or administration of a pharmaceutical composition comprising the Eg5 inhibitor to a subject, or application or administration of a pharmaceutical composition comprising the Eg5 inhibitor to an isolated tissue or cell line from a subject, who has a solid tumor or hematological cancer, a symptom associated with a solid tumor or hematological cancer, or a predisposition toward development of the solid tumor or hematological cancer, where the purpose is to cure, heal, alleviate, relieve, alter, remedy, ameliorate, improve, or affect the solid tumor or hematological cancer, any associated symptoms of the solid tumor or hematological cancer, or the predisposition toward development of the solid tumor or hematological cancer.

By "anti-tumor activity" is intended a reduction in the rate of malignant cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Therapy with at least one Eg5 inhibitor causes a physiological response that is beneficial with respect to treatment of solid tumors in a human. Therapy with at least one Eg5 inhibitor causes a physiological response that is beneficial with respect to treatment of hematological tumors in a human. It is recognized that the methods of the invention may be useful in preventing further tumor outgrowths arising during therapy.

By "therapeutically effective dose or amount" or "effective amount" is intended an amount of Eg5 inhibitor that, when administered brings about a positive therapeutic response with respect to treatment of a patient with a solid tumor or hematological cancer. It is recognized that the method of treatment may comprise a single administration of a therapeutically effective dose or multiple administrations of a therapeutically effective dose of the inhibitor.

Pharmaceutical compositions of several embodiment of the present invention comprise an effective amount of one or more agents of the present invention and, optionally, additional agents, dissolved or dispersed in or provided with a pharmaceutically acceptable carrier, for example. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one agent of the invention or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The agent of the invention may comprise different types of carriers depending on whether it is to be administered in solid, liquid or aerosol form, and whether it need to be sterile for such routes of administration as injection. Several embodiment of the present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, *Remington's Pharmaceutical Sciences,* 18th Ed. Mack Printing Company, 1990, incorporated herein by reference).

"Pharmaceutically acceptable salts" refers to the nontoxic acid or alkaline earth metal salts of the compounds of formula I and H. These salts can be prepared in situ during the final isolation and purification of the compounds of formula I and II, or by separately reacting the base or acid functions with a suitable organic or inorganic acid or base, respectively. Representative pharmaceutically acceptable salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfonate, ethanesulfonate, glucoheptanoate, glycerophosphate, hemi-sulfate, heptanoate, hexanoate, fumarate, hippurate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylpropionate, picrate, pivaloate, propionate, succinate, sulfate, tartrate, thiocyanate, p-toluenesulfonate and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides; arylalkyl halides like benzyl and phenethyl bromides, and others. Water or oil-soluble or dispersible products are thereby obtained.

A compound of the present invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with embodiments of the present invention, a composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing a method of one embodiment of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with an embodiment of the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle composition that include the agent of the invention, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of one or more embodiment of the present invention.

One of ordinary skill in the art would be familiar with the range of techniques that can be employed for dispersing a composition in a lipid vehicle. For example, the agent of the invention may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of certain embodiment of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Compounds

One embodiment of the present invention comprises a compound that inhibits a motor protein Eg5. The compound may be used as an anti-proliferation agent, an anti-cancer agent and/or an anti-tumor activity agent. One or more Eg5 inhibitors and a therapeutic agent described herein preferably cause cells to arrest during mitosis, eventually causing cell death by self-destruction (apoptosis). Embodiments of the current invention preferably comprise compositions and methods for making and using the compositions to inhibit Eg5. Eg5 inhibitors are preferably of the 2-amino-3-triarylmethylsulfanyl]-propan-1-ol scaffold. In one embodiment of the present invention, compounds described herein are screened for their ability to inhibit Eg5, preferably purified Eg5, and/or isolated Eg5 and/or to arrest cultured human tumor cells in mitosis.

Eg5 are ubiquitous in eukaryotic cells, with functional orthologs found in all animals, plants, fungi and slime molds. Eg5 orthologs in slime molds and unicellular fungi (organisms which do not break down their nuclear envelopes during mitosis) are not required for spindle pole separation, but instead play important roles in chromosome movements early in mitosis. However, in both plant and animal cells, this motor is critical for establishing spindle bipolarity. Embodiments of the present invention comprise methods of inhibiting these functions with a compound of the present invention or concentrations effective for such inhibition.

Although there have been few published studies of the actions of the known Eg5 inhibitors on invertebrate organisms, none of the inhibitors identified to date are functional in *Drosophila*, and comparison of the monastrol/STLC binding site between vertebrate- and *Drosophila* Eg5 reveal subtle differences in the binding pocket that introduce polar- and charged residues that preclude STLC binding to *Drosophila* Eg5 (known as Klp61-F). Thus, identification of Eg5 inhibitors that function in non-mammalian cells but do not in mammalian cells presents an opportunity for novel chemotherapeutics against fungal, protozoan, and animal pathogens. Examples include blood bourne pathogens such as *Trypanosoma* and *Plasmodium*, and intestinal parasites such as *Ascaris*. Disruption of Eg5 function would prevent those organisms from proliferating while having no effect on cell division in the host.

According to one embodiment of the present invention, compound 1.0 (2-amino-3-[(4-methoxy-phenyl)-diphenyl-methylsulfanyl]-propan-1-ol) and sometimes referred to herein as (MSTCO or NCl #76782) displays anti-proliferative activity towards a wide variety of tumor cell lines, with enhanced activity against cultured leukemia-, breast- and prostate cancer cell lines in vitro. This compound can also be provided as a therapeutic agent for treatment of proliferative disorders in general. This class of compounds may therefore have potential for use in chemotherapy against these and other cancers. These compounds may also have applications as therapeutics for other diseases and conditions that are characterized by uncontrolled cellular proliferation such as proliferation disorders. These compounds also have utility as molecular probes for biological and medical research in which specific inhibitors are used. Compound 1.0 (MSTCO) and related analogs have the capability of being evaluated as candidates for pre-clinical drug development, including additional structure-activity studies, evaluation of toxicity in normal and tumor cell lines, and evaluation of safety and efficacy in a murine model.

One embodiment of the present invention comprises a compound of formula I. The compound of formula I may be used as an agent for the treatment of cell proliferative diseases. The compound of formula I preferably has a structure where $R^1$ represents a substituted or unsubstituted aryl group, or a substituted or unsubstituted heterocyclic group; $R^2$ and $R^3$ can represent the same or different aryl or heteroaryl groups with respect to $R^1$; $(R^3)_n$, wherein n=0 or n=1, may be independently selected from a substituted or unsubstituted carbocyclic or heterocyclic groups, or a linear or branched alkenyl or alkyl substituent when n=1, that may also possess additional substituents, including all possible combinations of individual groups described herein; or $R^3$ may be absent when n=0; and $R^4$ may be a hydroxy group, an alkoxy group, an amino group, an alkylamino group, an arylamino or heteroaryl group, a fluoride, or other substituted derivatives, including a single ring or multiple condensed rings for example a monocyclic or 6-7 membered cyclic structures in which $R^3$ and $R^4$ are connected by covalent chemical bonds when n=1; or $R^4$ is covalently bonded with the substituted carbon when n=0 as illustrated in Formula II. The absolute stereochemistry of the $R^{1-4}$ positions may be enantiomerically pure S, or R, or may consist of racemic or scalemic mixtures. A preferred embodiment of the present invention is an Eg5 inhibitor containing a 2-amino-3-triarylmethylsulfanyl-propan-1-ol represented by compound 1.0 (MSTCO) or a pharmacologically acceptable salt thereof as an active ingredient.

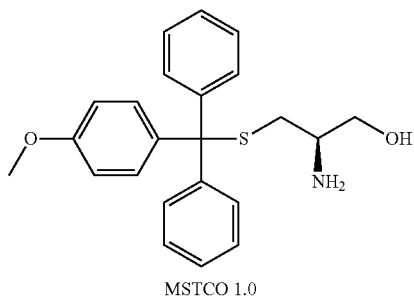

MSTCO 1.0

Formula I

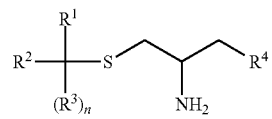

Formula II

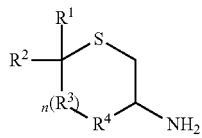

In an embodiment of the present invention, compound 1.0 (MSTCO) and related analogs are a cell-permeable and/or potentially orally available inhibitor with promise for application as a compound that can prevent proliferation of immortal cells and may have potential as a chemotherapeutic agent. These desirable physicochemical and inhibitory properties are associated with the substituted 2-amino-propan-1-ol structure. Compound 2.5 ((R)-2-amino-3-(tritylthio) propanoic acid, (STLC)) is a 2-amino-propanoic acid derivative and inhibits Eg5 in biochemical assays and has anti-proliferative activity. However, compound 2.5 (STLC) has poor membrane permeability and solubility and is therefore not an attractive candidate for use as a treatment in the clinical arena. One embodiment of the present invention provides an STLC analog with the amino- and tri-aryl-methyl groups of STLC retained, but incorporates a hydroxyl group in place of the carboxylic acid of STLC. The hydroxyl group helps negate the zwitterionic character of STLC. As a result, this embodiment provides compounds with improved cell-permeability, and/or water solubility, and/or meets preliminary requirements for orally-available drugs as determined by correlation to Lipinski rules when compared to STLC. Other derivatives including but not limited to heteroarylmethyl derivatives, 1-alkoxy-, 1-fluoro- and 1-amino propanes and analogs based on these compounds, as well as cyclic analogs incorporating a 2-amino-3-mercaptopropan-1-ol moiety also exhibit promising characteristics as cancer therapeutics and molecular probes.

Embodiments of the present invention comprise related compounds that incorporate a 2-amino-3-mercaptopropan-1-ol moiety. A representative group of these compounds have been synthesized and evaluated using biochemical, cell-based, and non-vertebrate animal models.

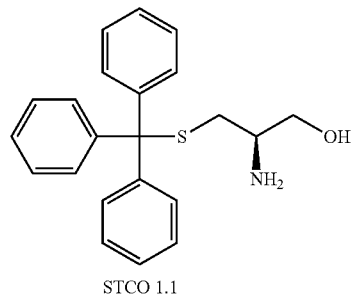

STCO 1.1

(R)-2-amino-3-(tritylthio)propan-1-ol
CAS Registry Number: 273401-69-7

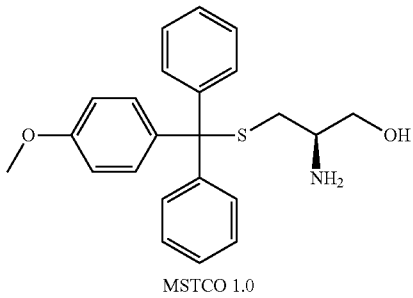

MSTCO 1.0

(R)-2-amino-3-(((4-methoxyphenyl)
diphenylmethyl)thio)propan-1-ol

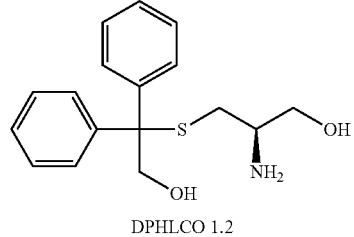

DPHLCO 1.2

(R)-2-amino-3-((2-hydroxy-1,1-
diphenylethyl)thio)propan-1-ol

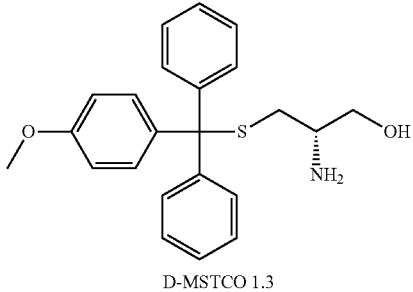

D-MSTCO 1.3

(S)-2-amino-3-(((4-methoxyphenyl)
diphenylmethyl)thio)propan-1-ol

The experimental conditions for the synthesis of the compounds of embodiments of the present invention, and the process for incorporating a 2-amino-3-mercaptopropan-1-ol moiety are described in the following examples. Compound 1.1 (STCO) and compound 1.0 (MSTCO) of Example 3 and Example 4 can also be synthesized by an alternative embodiment that preferably comprises reduction of cysteine derivatives compounds 2.5 and 2.6 (STLC and MSTLC) as described in Examples 3 and 4. Compound 1.3 (DPHLCO) can be synthesized by an alternative embodiment using a corresponding new cysteine derivative compound 3.7 (DPALC) as described in Example 6.

Additional embodiments of the present invention can comprise cyclic structures that incorporate a 2-amino-3-mercaptopropan-1-ol moiety into the compound of Formula II when $R^3$ is covalently bonded to the substituted carbon such as that represented by formulas II(a-h). Representative examples include when $R^4$ is an oxygen (O) that is covalently bonded to the diarylmethyl carbon atom to form 2,2-diaryl-1,3-oxathian-5-amine (Formula IIa); when $R^4$ is an oxygen (O) that is covalently bonded to a carbonyl (CO) to form a 3,3-diaryl-6-amino-1,4-oxathiepan-2-one (Formula IIb); when $R^4$ is an oxygen (O) that is covalently bonded to a carbon atom possessing additional alkyl substitutents $R^6$ and $R^7$ to form the 3,3-diaryl-1,4-oxathiepan-6-amine (Formula IIc); additionally substitutents $R^6$ and $R^7$ may consist of a carbocyclic or heterocyclic ring (Formula IId). Additional examples include when $R^4$ is a substituted nitrogen ($NR^5$) that is covalently bonded to the diarylmethyl carbon atom to form 2,2-diaryl-1,3-thiazinan-5-amine (Formula IIe); when $R^4$ is a substituted nitrogen ($NR^5$) that is covalently bonded to a carbonyl (CO) to form a 2,2-diaryl-6-amino-1,4-thiazepan-3-one (Formula IIf); when $R^4$ is a substituted nitrogen ($NR^5$) that is covalently bonded to a carbon atom possessing additional alkyl substitutents $R^6$ and $R^7$ to form the 2,2-diaryl-1,4-thiazepan-6-amine (Formula IIg); additionally substitutents $R^6$ and $R^7$ may consist of a carbocyclic or heterocyclic ring (Formula IIh).

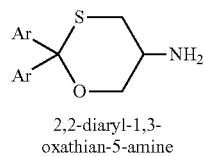

IIa 2,2-diaryl-1,3-oxathian-5-amine

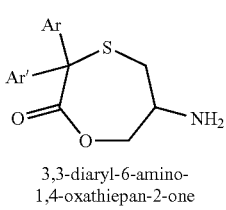

IIb 3,3-diaryl-6-amino-1,4-oxathiepan-2-one

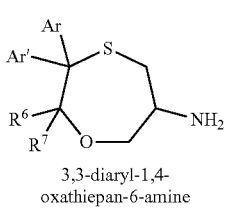

IIc 3,3-diaryl-1,4-oxathiepan-6-amine

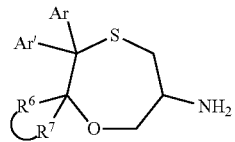

IId

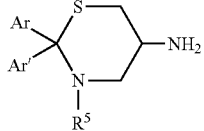

IIe 2,2-diaryl-1,3-thiazinan-5-amine

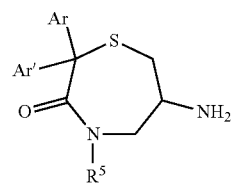

IIf 6-amino-2,2-diaryl-1,4-thiazepan-3-one

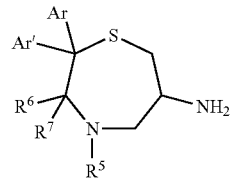

IIg 2,2-diaryl-1,4-thiazinan-6-amine

IIh

Another embodiment of the present invention comprises compounds comprising compound 2.2, ((R)-2-amino-3-mercaptopropanoic acid, (L-cysteine)). Some of the cysteine derivatives of this embodiment were obtained commercially when available or prepared by standard methodology. Other cysteine derivatives were synthesized by experimental procedures described in the examples. Compound 2.3 ((R)-4-((tritylthio)methyl) oxazolidine-2,5-dione (STLC-NCA) having CAS Registry Number: 1051374-19-6) and the related compound 2.4 ((R)-4-((((4-methoxyphenyl)diphenylmethyl)thio)methyl)oxazolidine-2,5-dione, (MSTLC-NCA)) were prepared and used for the synthesis of some cysteine derivatives of this embodiment of the present invention. Two additional cysteine derived compound 7.6 (MSTLCB-Sepharose) and compound 7.7 (MASTC-Sepharose) were synthesized as solid-phase affinity probes to evaluate the binding specificity of Eg5 for this class of carboxamide derivatives using pull-down assays and identification of the isolated protein (see Examples 20-22).

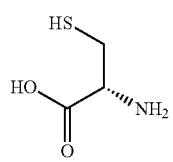

L-(R)-cysteine 2.2
(R)-2-amino-3-
mercaptopropanoic acid

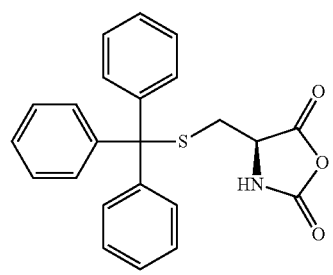

STLC-NCA 2.3
(R)-4-((tritylthio)methyl)
oxazolidine-2,5-dione
CAS Registry Number: 1051374-19-6

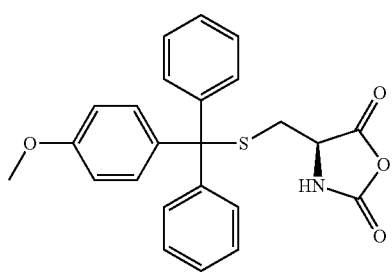

MSTLC-NCA 2.4
(R)-4-((((4-methoxphenyl)diphenylmethyl
thio)methyl)oxazolidine-2,5-dione Referring now to Table 1, cysteine derivatives synthesized for the characterization of EG5 binding and inhibition of Eg5 are illustrated.

TABLE 1

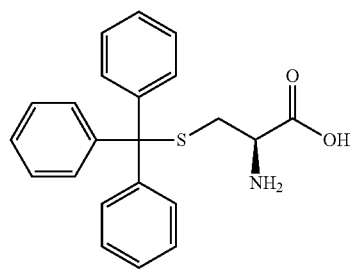

STLC 2.5
(R)-2-amino-3-(tritylthio)
propanoic acid

TABLE 1-continued

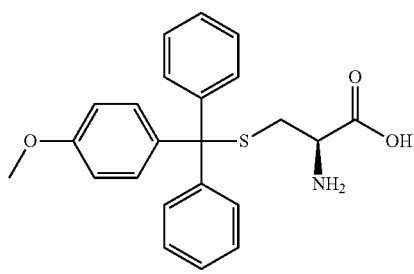 [SMILES: COc1ccc(C(SC[C@H](N)C(=O)O)(c2ccccc2)c2ccccc2)cc1]

MSTLC 2.6
(R)-2-amino-3-(((4-methoxyphenyl)
diphenylmethyl)thio)propanoic acid

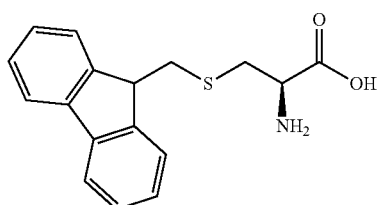

SFMC 2.7
(R)-3-(((9H-fluoren-9-yl)methyl)thio)-
2-aminopropanoic acid

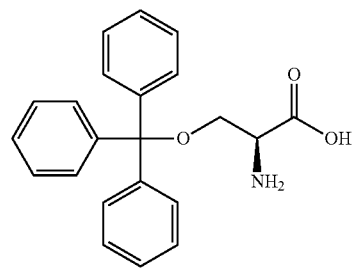 [SMILES: N[C@@H](COC(c1ccccc1)(c1ccccc1)c1ccccc1)C(=O)O]

OTC 2.8
(S)-2-amino-3-(trityloxy)
propanoic acid

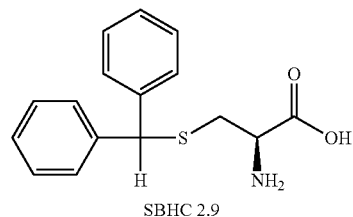

SBHC 2.9
(R)-2-amino-3-(benzhydrylthio)
propanoic acid

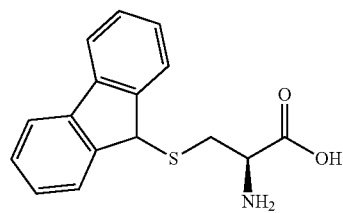 [SMILES: N[C@@H](CSC1c2ccccc2-c2ccccc21)C(=O)O]

SFC 3.0
(R)-3-((9H-fluoren-9-yl)thio)-
2-aminopropanoic acid

TABLE 1-continued

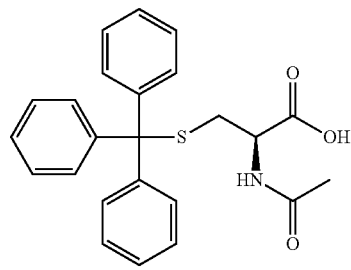 [SMILES: CC(=O)N[C@@H](CSC(c1ccccc1)(c1ccccc1)c1ccccc1)C(=O)O]

ASTC 3.1
(R)-2-acetamido-3-(tritylthio)
propanoic acid
CAS Registry Number: 27486-87-9
N-acetyl-S-(triphenylmethyl)-L-Cysteine

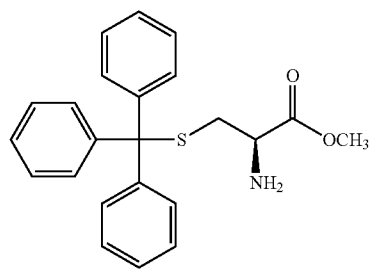 [SMILES: COC(=O)[C@@H](N)CSC(c1ccccc1)(c1ccccc1)c1ccccc1]

STCM 3.2
(R)-methyl 2-amino-3-
(tritylthio)propanoate

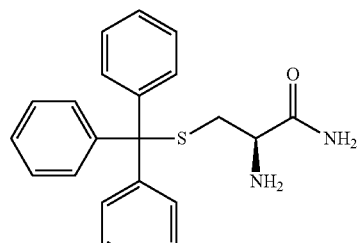

STCC 3.3
(R)-2-amino-3-(tritylthio)
propanamide
CAS Registry Number: 166737-85-5

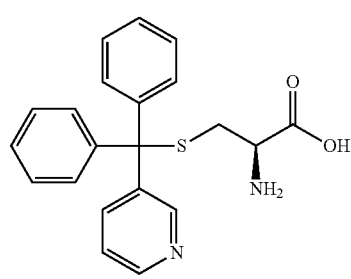 [SMILES: N[C@@H](CSC(c1ccccc1)(c1ccccc1)c1cccnc1)C(=O)O]

S3PTLC 3.4
(R)-2-amino-3-((diphenyl(pyridin-3-yl)
methyl)thio)propanoic acid

TABLE 1-continued

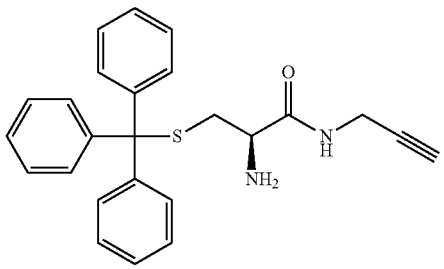 [SMILES: C#CCNC(=O)[C@@H](N)CSC(c1ccccc1)(c1ccccc1)c1ccccc1]

STPY 3.5
(R)-2-amino-N-(prop-2-yn-1-yl)-
3-(tritylthio)propanamide

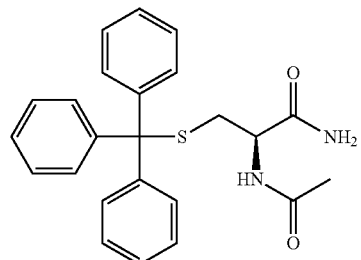

ASTCC 3.6
(R)-2-acetamido-3-
(tritylthio)propanamide

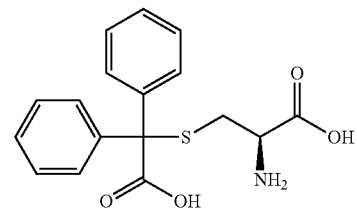 [SMILES: N[C@@H](CSC(C(=O)O)(c1ccccc1)c1ccccc1)C(=O)O]

DPALC 3.7
(R)-2-amino-3-((carboxydiphenyl-
methyl)thio)propanoic acid

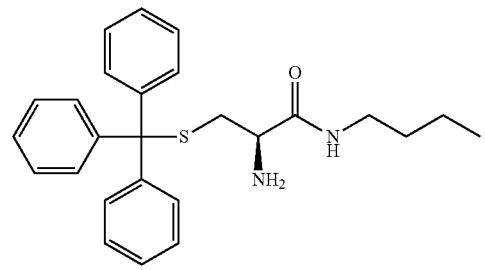 [SMILES: CCCCNC(=O)[C@@H](N)CSC(c1ccccc1)(c1ccccc1)c1ccccc1]

STCB 3.8
(R)-2-amino-N-butyl-3-
(tritylthio)propanamide

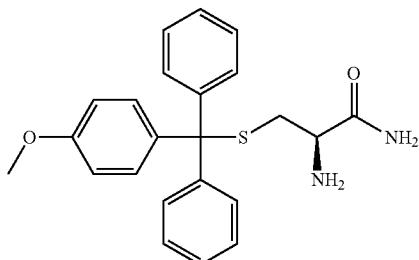

MASTC 3.9
(R)-2-amino-3-(((4-methoxyphenyl)
diphenylmethyl)thio)propanamide

TABLE 1-continued

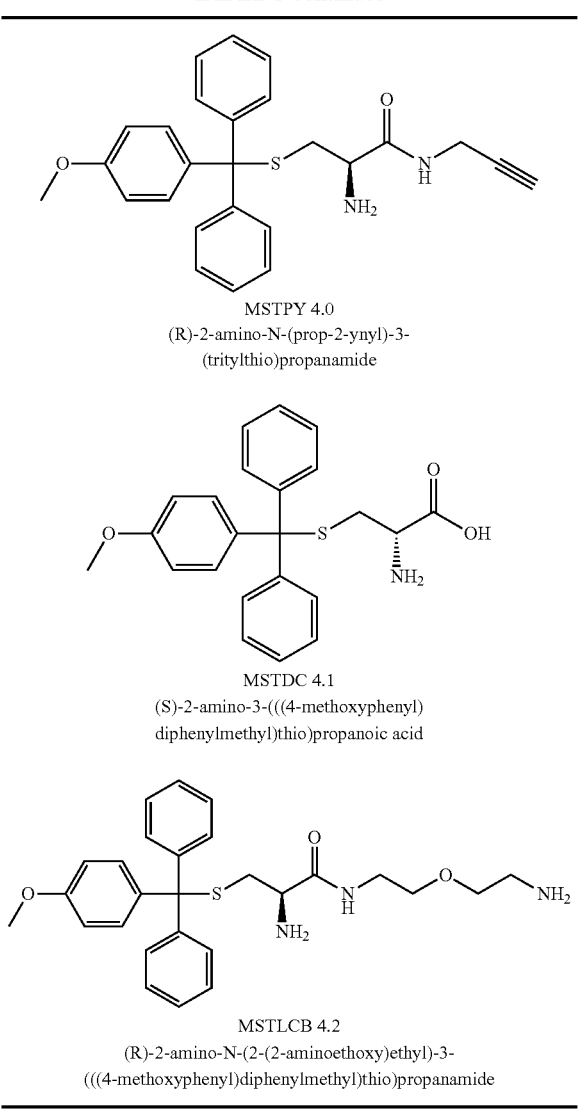

MSTPY 4.0
(R)-2-amino-N-(prop-2-ynyl)-3-(tritylthio)propanamide

MSTDC 4.1
(S)-2-amino-3-(((4-methoxyphenyl)diphenylmethyl)thio)propanoic acid

MSTLCB 4.2
(R)-2-amino-N-(2-(2-aminoethoxy)ethyl)-3-(((4-methoxyphenyl)diphenylmethyl)thio)propanamide

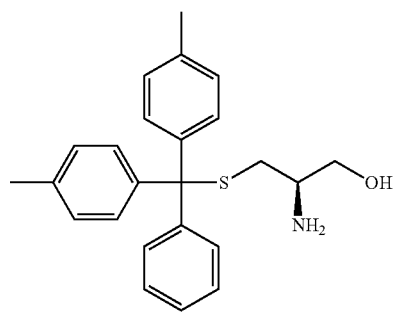
4.3

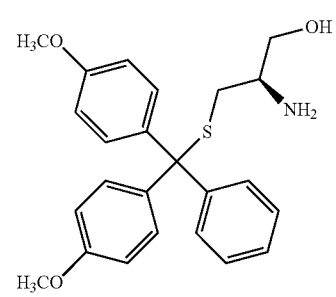
4.4

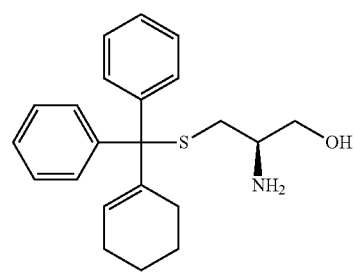
4.5

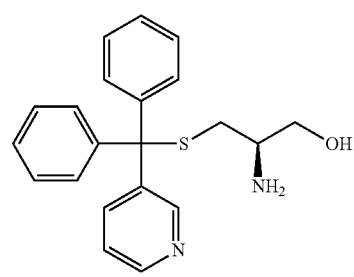
4.6

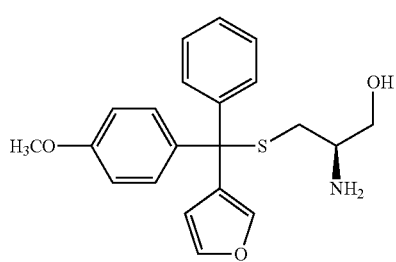
4.7

Another embodiment of the present invention comprises compounds having substitutions of formula I. These compounds are illustrated as compounds 4.3 to 6.4. These compounds preferably optimize the physicochemical properties of formula I for increased activity and/or specificity of Eg5 binding and/or inhibition, and/or improved water solubility, and/or permeability and/or pharmacological properties. Compounds 4.3 to 5.0 incorporate additional substitutions on the aryl groups by replacement of carbon atoms in the triarylmethyl entity of formula I with heteroatoms such as nitrogen, oxygen and sulfur, as well as replacement with other aryl, heteroaryl, alkyl, cycloalkyl, heterocyclic, as represented by the 2-pyridyl derivatives shown. Multiple heteroatom substitutions and varying the positions of substitution about each aromatic ring are also representative of compounds 4.3 to 5.0. Compounds 5.1 to 5.6 are based on additional substitutions of the $R^4$ group of formula I or of the propan-1-ol group to provide analogs including but not limited to the fluoro, hydroxyethyl, and amino-substituted analogs. Compounds 1.4 to 2.1 and 5.7 to 6.4 are based on cyclic structures representing formula II derived from the 2-amino-3-mercaptopropan-1-ol moiety.

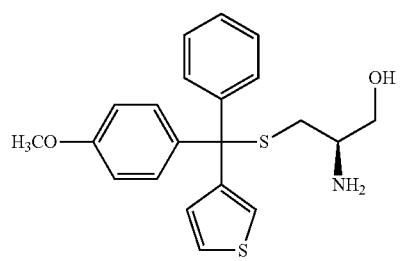
4.8
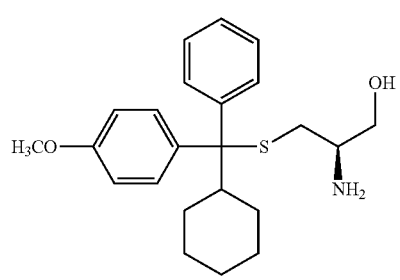
4.9
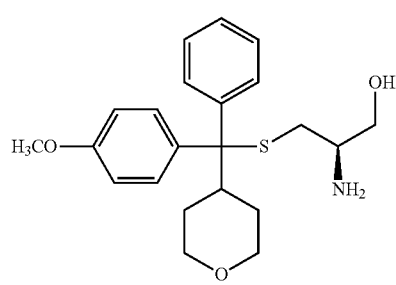
5.0
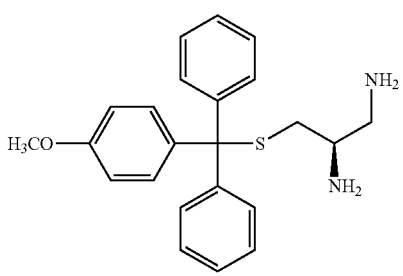
5.1
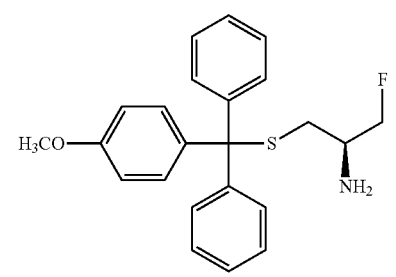
5.2
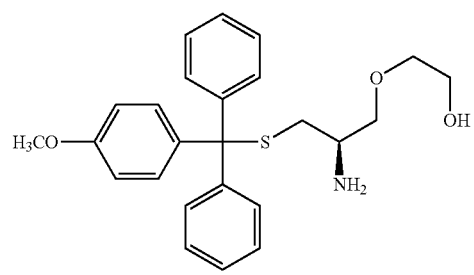
5.3
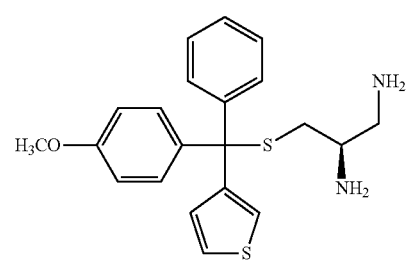
5.4
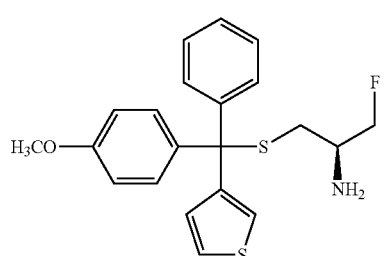
5.5
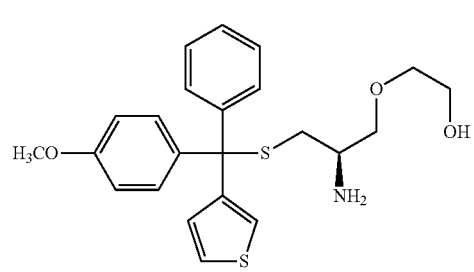
5.6
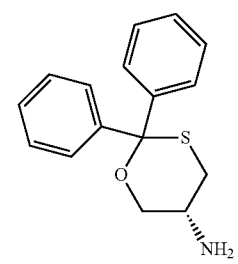
(R)-2,2-diphenyl-1,3-oxathian-5-amine
1.4

-continued

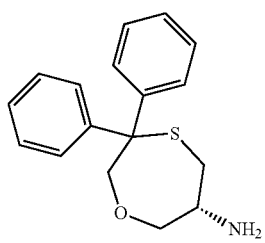

(R)-3,3-diphenyl-1,4-
oxathiepan-6-amine

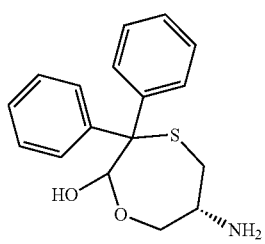

(6R)-6-amino-3,3-diphenyl-
1,4-oxathiepan-2-ol

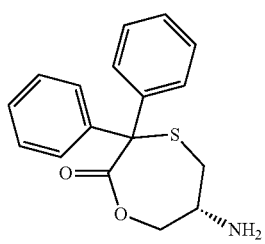

(R)-6-amino-3,3-diphenyl-
1,4-oxathiepan-2-one

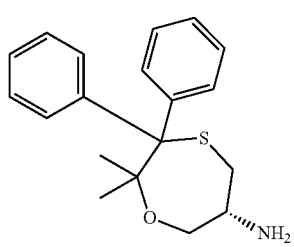

(R)-2,2-dimethyl-3,3-diphenyl-
1,4-oxathiepan-6-amine

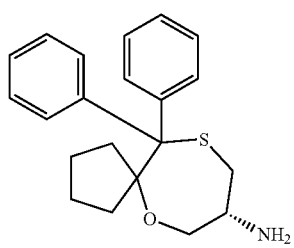

(R)-11,11-diphenyl-6-oxa-10-
thiaspiro[4.6]undecan-8-amine

-continued

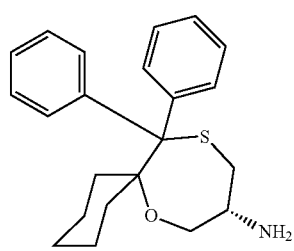

(R)-12,12-diphenyl-7-oxa-11-
thiaspiro[5.6]dodecan-9-amine

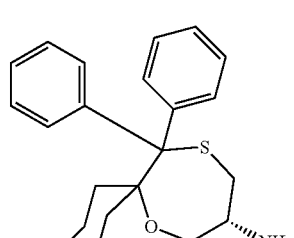

(R)-12,12-diphenyl-3,7-dioxa-11-
thiaspiro[5.6]dodecan-9-amine

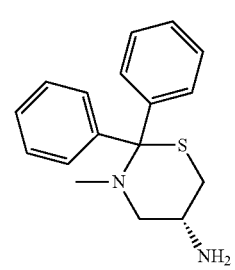

(R)-3-methyl-2,2-
diphenyl-1,3-thiazinan-
5-amine

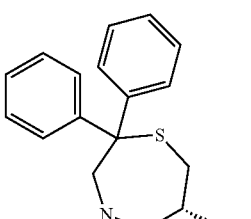

(R)-4-methyl-2,2-
diphenyl-1,4-thiazepan-
6-amine

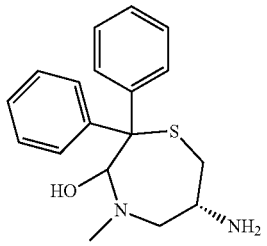

(6R)-6amino-4-methyl-
2,2-diphenyl-1,4-thiazepan-3-ol 1.5

1.6

1.7

1.8

1.9

2.0

2.1

5.7

5.8

5.9

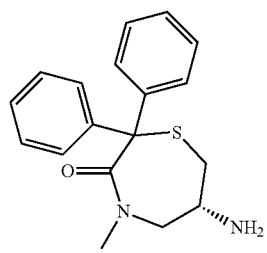

(R)-6-amino-4-methyl-
2,2-diphenyl-1,4-thiazepan-3-one

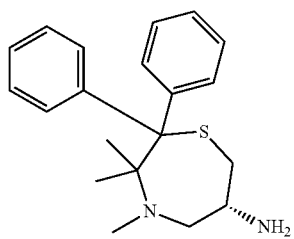

(R)-3,3,4-trimethyl-2,2-
diphenyl-1,4-thiazepan-
6-amine

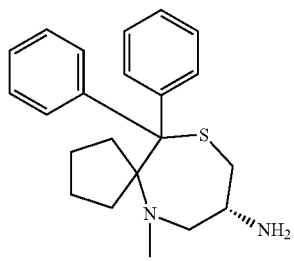

(R)-6-methyl-11,11-
diphenyl-10-thia-6-
azaspiro[4.6]undecan-
8-amine

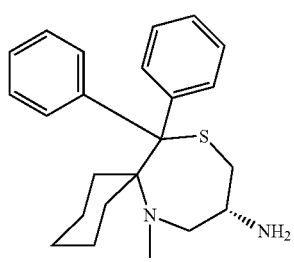

(R)-7-methyl-12,12-
diphenyl-11-thia-7-
azaspiro[5.6]dodecan-
9-amine

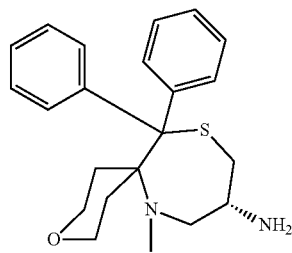

(R)-7-methyl-12,12-
diphenyl-3-oxa-11-thia-7-
azaspiro[5.6]dodecan
9-amine

Synthesis

Additional embodiments of the present invention comprise methods for synthesizing compounds that incorporate a 2-amino-3-mercaptopropan-1-ol moiety. The methods preferably comprise a reduction of 2-amino-3-mercaptopropanoic acid using excess borane ($BH_3$) reagent in an organic solvent such as tetrahydrofuran (THF) using an inert (oxygen-free) atmosphere such as argon or nitrogen to avoid oxidation of the thiol group, followed by quenching the excess borane reagent with an appropriate reagent such as dimethylformamide (DMF) that can then be incorporated directly into synthetic processes to produce one or more compounds.

The following examples are for illustrative purposes only and in no way limit embodiments of the present invention.

EXAMPLE 1

Synthesis of Cysteine Derivatives

All reactions were performed in an efficient fume hood. Solvents and reagents were purchased from commercial sources and were used without further purification. Compound 2.5 (STLC) (Novabiochem), was purchased from a commercial source, and compound 1.0 (MSTLC) was prepared by the reported procedures. (Naohisa Ogo, et al. (2007). *Synthesis and biological evaluation of l-cysteine derivatives as mitotic kinesin Eq5 inhibitors*; Bioorganic & Medicinal Chemistry Letters 17, 3921-3924; E. K. Weisburger, et al. (1964). Notes. Journal of the Chemical Society 515-18; and Yan Zheng, et al. (2006). *A Magnetic Biomimetic Nanocatalyst for Cleaving Phosphoester and Carboxylic Ester Bonds under Mild Conditions*. Organic Letters 8, 3215-3217 for details on preparations of the compounds).

Air sensitive reagents were stored in a glove box and handled according to accepted procedure. Chromatography was performed using ethyl acetate/hexanes (EtOAc/hex) or methanol/dichloromethane (MeOH/$CH_2Cl_2$) as eluent under medium pressure flash chromatography using Sorbent technologies prepacked columns. Dueterated solvents were used without further purification. NMR spectra were acquired at ambient temperatures (about 18±2° C.) unless otherwise noted. The $^1$H NMR spectra in $CDCl_3$ were referenced to TMS unless otherwise noted. The 13C {1H} NMR spectra were recorded at 75 or 100 MHz and referenced relative to the 13C {1H} peaks of the solvent. Spectra are reported as (ppm), (multiplicity, coupling constants (Hz), and number of protons). Infrared spectra were recorded as KBr pellets or neat films and are reported in $cm^{-1}$. HPLC-MS was performed using a Symmetry C18 (5 mm, 3.0×150 mm, Waters) column. Analytical HPLC was obtained using Waters 2695 with Waters2996 Photodiode Array (PDA) and Micromass ZQ ESI-MS detection (cone voltage 62V, Capillary Voltage 3 kV). L). The compound (1 mg/mL $CH_3CN$, 20 μL) was injected into Waters Symmetry® C18 5 μm 3.0×150 mm column eluted with $CH_3CN/H_2O$ as specified.

EXAMPLE 2

Scheme A illustrates the reduction of a cysteine (2-amino-3-mercaptopropanoic acid) in which the amine group has been protected as a carbamate derivative to generate the corresponding carbamate protected 2-amino-3-mercaptopropan-1-ol. The carbamate decreases the basicity and nucleophilicity of the amine group, and makes the derivative more soluble in organic solvents. The resulting derivative may be used advantageously in a variety of synthetic procedures designed to incorporate the 2-amino-3-mercaptopropan-1-ol moiety to produce compounds of Formula I, particularly in cases where the unprotected amine group would have unfavorable reactivity, poor solubility in organic solvents, or other associated complications that would adversely affect the synthesis of the target compounds. The thiol group of the protected derivative can be used to form new carbon-sulfur bonds. The protection of the amine may also be advantageous for additional chemical modifications of the alcohol group, including the formation of carbon-oxygen bonds, carbon-nitrogen bonds, carbon-fluorine and other related substitution reactions. Other protecting groups may be substituted for the carbamate as described herein but are not limited thereto.

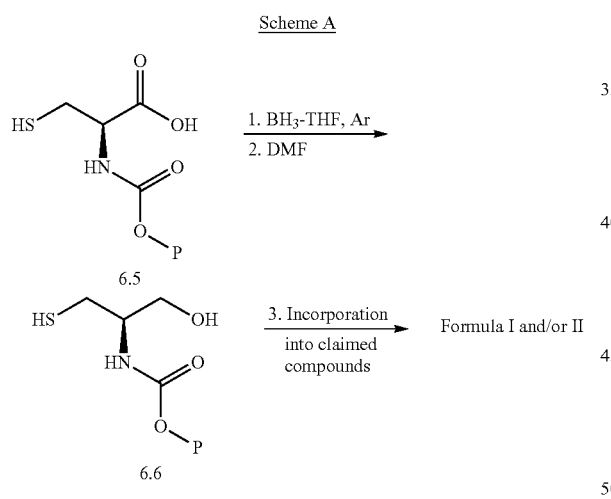

Scheme A

This method may also be suitable for amine-derivatives of 2-amino-3-mercaptopropan-1-ol that include common amine protecting groups as represented by Formula I in which P represents standardized carbamate protecting groups such as tert-butyl (`Boc), benzyl (Cbz), (9H-fluoren-9-yl)methyl (Fmoc) and others as known to those skilled in the art. Each of these carbamate protecting groups can be removed using different reaction conditions that are readily recognized by practitioners of the art, which can be advantageous depending on the identify of other potentially reactive functional groups and other chemically sensitive derivatives.

One embodiment of the present invention is represented in Scheme B by the preparation of (R)-(9H-fluoren-9-yl)methyl 1-hydroxy-3-mercaptopropan-2-ylcarbamate (6.8). This modification may provide added synthetic utility and versatility for incorporation of a 2-amino-3-mercaptopropan-1-ol moiety into synthetic processes that produce the compounds of embodiments of the present invention. The Fmoc protecting groups can then be removed using organic amine bases such as piperidine as standard reagents and conditions that are generally known to those skilled in the art. These mild basic conditions would be advantageous when the use of acidic reagents would cause decomposition.

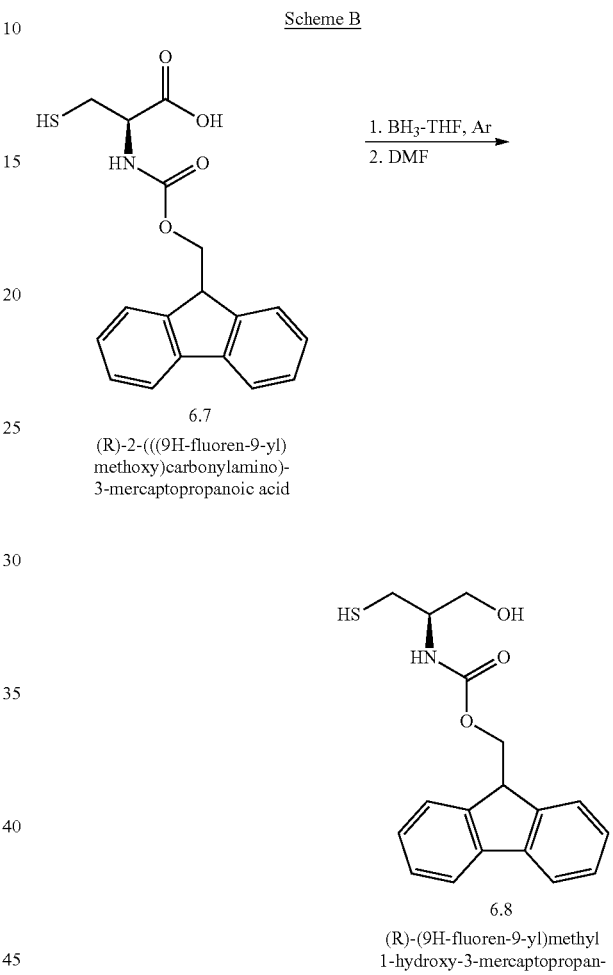

Scheme B

This method may also be suitable for using amine-protected disulfide compounds, such as those derived from L-(R)-, D-(S)-, and DL-cystine derivatives as represented by formulas IIa-h, and for example of the Fmoc-L-cystine derivative compound 7.0 [(5R,10R)-1,14-di(9H-fluoren-9-yl)-3,12-dioxo-2,13-dioxa-7,8-dithia-4,11-diazatetradecane-5,10-dicarboxylic acid]. In this embodiment, the disulfide bond is preferably cleaved to yield a free thiol using suitable reducing agents that are generally known to those skilled in the art, including thiol-containing reagents such as, for example, mercaptoethanol, mercaptoethylamine, and dithiothreitol, hydride reagents such as sodium borohydride ($NaBH_4$), and phosphine reagents such as tris(2-carboxyethyl) phosphine (TCEP), to provide another route for preparing carbamate-protected 2-amino-3-mercaptopropan-1-ol derivatives illustrated in Schemes A and B.

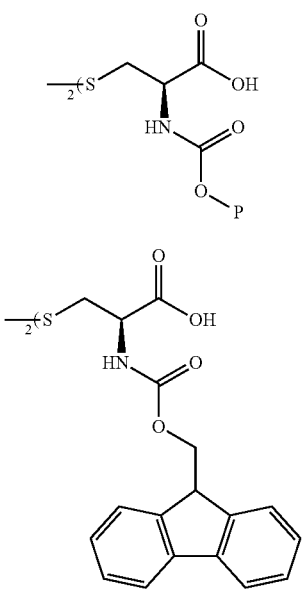

EXAMPLE 3

Synthesis of Compound 1.0 (MSTCO)

Scheme C

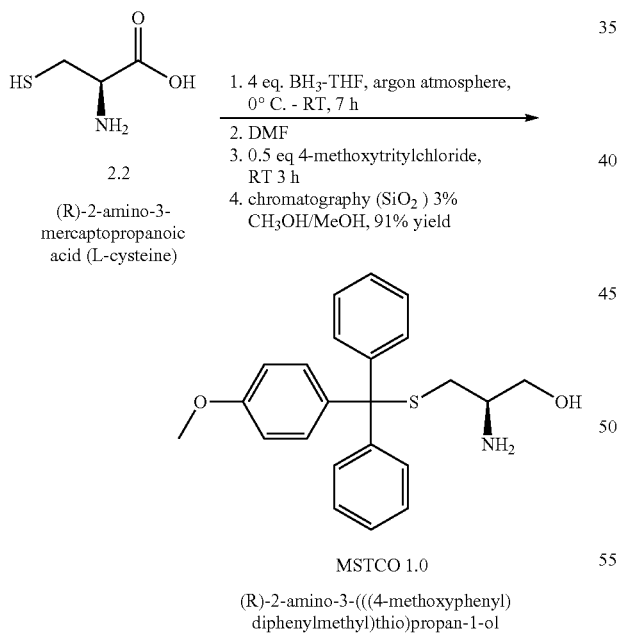

Borane-THF (20 mL, 20 mmol) was added to compound 2.2 (L-cysteine) (0.605 g, 5 mmol) in dry THF (25 mL) under an argon atmosphere at 0° C., then allowed to stir at room temperature for 7 h as is illustrated in Scheme C. The reaction mixture was quenched with dry DMF (5 mL) and stirred for 1 h. 4-Methoxytrityl chloride (0.771 g, 2.5 mmol) was added to the reaction mixture and stirred at room temperature for 3 h. The volatiles were removed in vacuo and the residue treated with water (100 mL) and the crude product was extracted with methylene chloride (100 mL). The organic layer was washed with saturated sodium chloride solution (30 mL), and dried over anhydrous sodium sulfate. The solvents were evaporated under reduced pressure and the residue was purified by silica gel chromatography using methanol/methylene chloride (03:97) as eluent to obtain the pure product, MSTCO (0.855 g, 91%) as colorless viscous oil. IR (Neat, cm$^{-1}$): 3447, 2925, 1508, 1250, 1033. $^1$H (300 MHz, CDCl$_3$) δ 7.42-7.17 (m, 12H), 6.83-6.77 (m, 2H), 3.78 (s, 3H), 3.44-3.39 (dd, J=4.25, 4.25 (10.71, 4.11 Hz, 1H), 3.21-3.15 (m, 1H), 2.65-2.55 (m, 1H), 2.36-2.19 (m, 2H), 1.74 (s, 3H); $^{13}$C NMR (75 MHz, CDCl$_3$) δ 158.10, 144.95, 136.70, 130.72, 129.46, 127.87, 126.67, 113.14, 66.36, 65.72, 55.20, 52.06, 36.81. HPLC-MS: Elution with 20-80% CH$_3$CN in H$_2$O (gradient 1.5% min$^{-1}$), exhibited a single peak at 2.18 min. ESI-MS m/z [ESA] calcd for C$_{29}$H$_{26}$NO$_2$S [M+H]$^+$380.09; found 380.16). HRMS calcd 380.1679, observed: 380.1678

Alternative synthesis of compound 1.0 (MSTCO) by reduction of cysteine derivative compound 2.6 (MSTLC) with borane is illustrated in Scheme C.1.

Scheme C.1

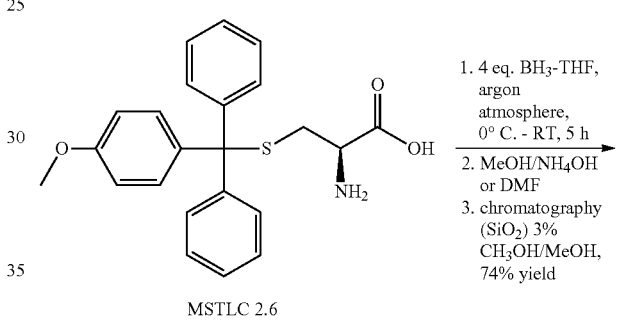

Borane-THF (about 5 mL, 5 mmol, 1M) solution was added dropwise to compound 2.6 (MSTLC) (about 0.393 g, 1 mmol) in dry THF (about 5 mL) at approximately 0° C. under argon, and allowed to stir at room temperature for about 3.5 h. The reaction was quenched slowly with about 5 mL of deionized water, then evaporated and dried in vacuo. The reaction mixture was diluted with about 10 mL of deionized water, extracted with CH$_2$Cl$_2$, dried over anhydrous Na$_2$SO$_4$, and evaporated to obtain a crude solid. The crude product was heated at approximately 60° C. with 4 M NaOH (about 1 mL) in methanol (about 3 mL) for about 3 hours and the volatiles were removed by rotary evaporation. The crude reaction mixture was purified by silica gel column chromatography using MeOH/CH$_2$Cl$_2$ (5:95) to isolate the product as colorless solid (about 0.290 g, 74%). FT-IR (KBr): 3447, 2925, 1508, 1250, 1033 cm$^{-1}$. $^1$H (300 MHz, CDCl$_3$): δ 7.42-7.17 (m, 12H), 6.83-6.77 (m, 2H), 3.78 (s, 3H), 3.44-3.39 (dd, J=10.71, 4.11

Hz, 1H), 3.21-3.15 (m, 1H), 2.65-2.55 (m, 1H), 2.36-2.19 (m, 2H), 1.74 (s, 3H). $^{13}$C NMR (300 MHz, CDCl$_3$): δ 158.10, 144.95, 136.70, 130.72, 129.46, 127.87, 126.67, 113.14, 66.36, 65.72, 55.20, 52.06, 36.81. HPLC-MS (ES$^+$) m/z: 380.09 (MH$^+$, C$_{29}$H$_{26}$NO$_2$S requires 380.16).

EXAMPLE 4

Synthesis of Compound 1.3 (D-MSTCO)

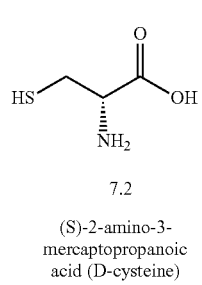

7.2

(S)-2-amino-3-mercaptopropanoic acid (D-cysteine)

Scheme D 1. 4 eq. BH$_3$-THF, argon atmosphere, 0° C. - RT, 7 h
2. DMF
3. 0.5 eq 4-methoxytritylchloride, RT 3 h
4. chromatography (SiO$_2$) 3% CH$_3$OH/MeOH, 92% yield

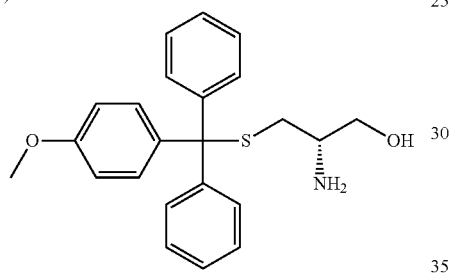

D-MSTCO 1.3

(S)-2-amino-3-(((4-methoxyphenyl)diphenylmethyl)thio)propan-1-ol

Borane-THF (5 mL, 5 mmol) was added to compound 7.2 D-cysteine (0.121 g, 1 mmol) in dry THF (5 mL) under an argon atmosphere and cooled at 0° C., then allowed to stir at room temperature for 7 h as is illustrated in Scheme D. The reaction mixture was quenched with dry DMF (1 mL) and stirred for 1 h. 4-Methoxytrityl chloride (0.771 g, 2.5 mmol) was added to the reaction mixture and stirred at room temperature for 3 h. The volatiles were removed in vacuo and the residue treated with water (20 mL) and the crude product was extracted with methylene chloride (20 mL). The organic layer was washed with saturated sodium chloride solution (10 mL), and dried over anhydrous sodium sulfate. The solvents were evaporated under reduced pressure and the residue was purified by silica gel chromatography using methanol/methylene chloride (03:97) as eluent to obtain the pure product compound 1.3 D-MSTCO (0.351 g, 92%) as colorless viscous oil. [α]$^{20}_D$ −6.5° (c 0.57, CHCl$_3$). IR (Neat, cm$^{-1}$): 3447, 2925, 1508, 1250, 1033. $^1$H (300 MHz, CDCl$_3$) δ 7.42-7.17 (m, 12H), 6.83-6.77 (m, 2H), 3.78 (s, 3H), 3.44-3.39 (dd, J=10.71, 4.11 Hz, 1H), 3.21-3.15 (m, 1H), 2.65-2.55 (m, 1H), 2.36-2.19 (m, 2H), 1.74 (s, 3H); $^{13}$C NMR (75 MHz, CDCl$_3$) δ 158.10, 144.95, 136.70, 130.72, 129.46, 127.87, 126.67, 113.14, 66.36, 65.72, 55.20, 52.06, 36.81. HPLC-MS: Elution with 20-80% CH$_3$CN in H$_2$O (gradient 1.5% min$^{-1}$), exhibited a single peak at 2.18 min. ESI-MS m/z [ES+] calcd for C$_{29}$H$_{26}$NO$_2$S [M+H]$^+$380.09; found 380.16).

EXAMPLE 5

Synthesis of Compound 1.1 (STCO)

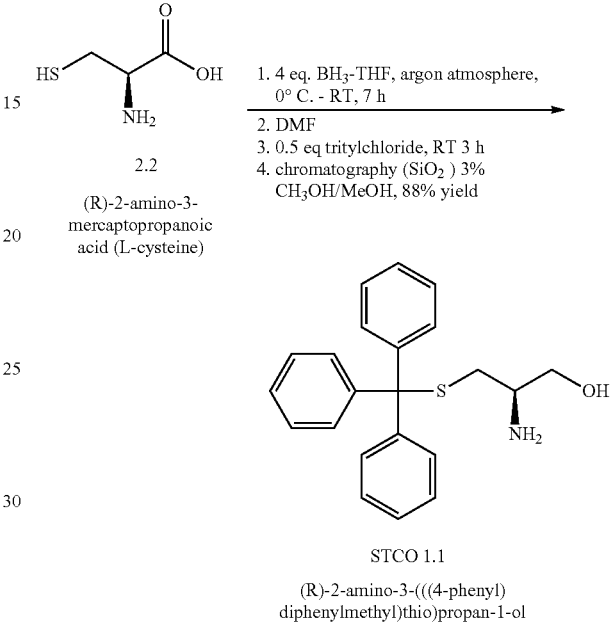

Scheme E 2.2

(R)-2-amino-3-mercaptopropanoic acid (L-cysteine)

1. 4 eq. BH$_3$-THF, argon atmosphere, 0° C. - RT, 7 h
2. DMF
3. 0.5 eq tritylchloride, RT 3 h
4. chromatography (SiO$_2$) 3% CH$_3$OH/MeOH, 88% yield

STCO 1.1

(R)-2-amino-3-(((4-phenyl)diphenylmethyl)thio)propan-1-ol

Borane-THF (4 mL, 4 mmol) was added to compound 2.2 (L-cysteine) (0.121 g, 1 mmol) in dry THF (5 mL) under an argon atmosphere and cooled at 0° C., then allowed to allowed to stir at room temperature for 7 h as is illustrated in Scheme E. The reaction mixture was quenched with dry DMF (1 mL) and stirred for 1 h. Tritylchloride (0.139 g, 0.5 mmol) was added to the reaction mixture and stirred at room temperature for 3 h. The volatiles were removed in vacuo and the residue treated with water (20 mL) and the crude product was extracted with methylene chloride (20 mL). The organic layer was washed with saturated sodium chloride solution (10 mL), and dried over anhydrous sodium sulfate. The solvents were evaporated under reduced pressure and the residue was purified by silica gel chromatography using methanol/methylene chloride (03:97) eluent to obtain the pure product compound 1.1 (STCO) (0.153 g, 88%) as a colorless viscous oil. IR (KBr, cm$^{-1}$): 3425, 3054, 2917, 1593, 742. $^1$H NMR (300 MHz, CDCl$_3$) δ 7.43-7.39 (m, 6H), 7.31-7.17 (m, 9H), 3.38 (dd, J=10.86, 4.26 Hz, 1H), 3.15 (dd, J=10.71, 6.89 Hz, 1H), 2.61-2.53 (m, 1H), 2.31 (dd, J=12.47, 5.14 Hz, 1H), 2.20 (dd, J=12.47, 7.63 Hz, 1H), 1.93 (s, 3H); $^{13}$C NMR (75 MHz, CDCl$_3$) δ 144.61, 129.50, 127.84, 126.67, 66.77, 65.53, 51.99, 36.62. HPLC-MS: Elution with 20-80% CH$_3$CN in H$_2$O (gradient 1.5% min$^{-1}$), exhibited a single peak at 3.92 min. ESI-MS m/z [ES+] calcd for C$_{22}$H$_{24}$NOS [M+H]$^+$ 350.44; found 350.16.

An alternative synthesis of compound 1.1 (STCO) by reduction of cysteine derivative compound 2.5 (STLC) as is illustrated in Scheme F. Borane-THF (about 4.5 mL, 4.5 mmol, 1M) solution was added to compound 2.5 (STLC) (approximately 0.363 g, 1 mmol) in dry THF (about 8 mL) at about 0° C., and allowed to stir at room temperature for about 4.5 h. The reaction mixture was concentrated and the residue was stirred with aqueous ammonia (about 1.5 mL) in MeOH (about 5 mL) at room temperature for about 12 hours. The volatiles were removed in vacuo, and the residue was chromatographed using MeOH/CH$_2$Cl$_2$ (5:95) as eluent to isolate the pure product as colorless solid (about 0.261 g, 74%). FT-IR (KBr): 3425, 3054, 2917, 1593, 742 cm$^{-1}$. $^1$H NMR (300 MHz, CDCl$_3$): δ 7.43-7.39 (m, 6H), 7.31-7.17 (m, 9H), 3.38 (dd, J=10.80, 4.26 Hz, 1H), 3.15 (dd, J=10.80, 6.89 Hz, 1H), 2.61-2.53 (m, 1H), 2.31 (dd, J=12.47, 5.14 Hz, 1H), 2.20 (dd, J=12.47, 7.63 Hz, 1H), 1.93 (s, 3H). $^{13}$C NMR (75 MHz, CDCl$_3$): δ 144.61, 129.50, 127.84, 126.67, 66.77, 65.53, 51.99, 36.62. HPLC-MS (ES$^+$) m/z: 350.44 (MH$^+$, C$_{22}$H$_{24}$NOS requires 350.16).

Compound 1.1 ((STCO) having CAS Registry Number: 273401-69-7) can also be prepared by reduction of the corresponding carboxylic acid with sodium borohydride, and used as an intermediate in the synthesis of ligands for iridium catalysts. (Danielle G. Petra, et al., Aminosulf(ox)ides as Ligands for Iridium(I)-Catalyzed Asymmetric Transfer Hydrogenation, J. Org. Chem. (2000), 65(10), 3010-3017).

EXAMPLE 6

Synthesis of compound 1.2 (DPHLCO) by reduction of cysteine derivative compound 3.7 (DPALC)

Scheme F

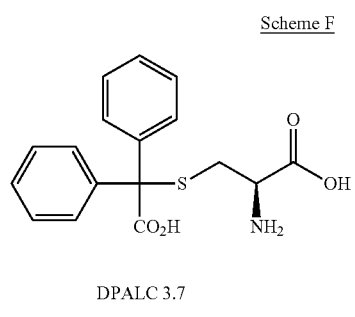

DPALC 3.7

(R)-2-amino-3-(carboxydiphenyl-methylthio)propanoic acid

1. BH$_3$-THF, argon atmosphere, 0° C. - RT, 16 h
2. DMF
3. chromatography (SiO$_2$ ) 10% CH$_3$OH/MeOH, 30% yield

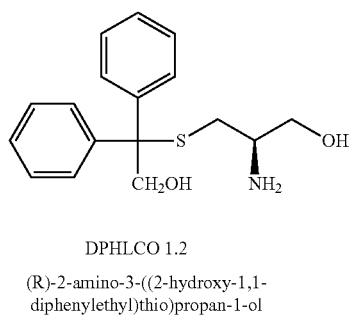

DPHLCO 1.2

(R)-2-amino-3-((2-hydroxy-1,1-diphenylethyl)thio)propan-1-ol

Borane-THF (2 mL, 2 mmol) solution was added dropwise to compound 3.7 (DPALC) (0.08 g, 0.24 mmol) in dry THF (2 mL) at 0° C. under argon, and allowed to stir at room temperature for 16 h as is illustrated in Scheme E. The reaction mixture was quenched with dry DMF (0.2 mL) and allowed to stir at room temperature for 1 h. Volatiles were removed in vacuo and dried to get the crude residue. The residue was purified by silica gel column chromatography using MeOH/CH$_2$Cl$_2$ (10:90) to isolate the product as thick oil (0.022 g, 30%). IR (KBr, cm$^{-1}$): IR (Neat, cm$^{-1}$): 3334, 3056, 2928, 1597, 1068. $^1$H (300 MHz, CD$_3$OD) δ 7.43-7.40 (m, 4H), 7.32-7.23 (m, 6H), 4.29 (s, 2H), 3.49-3.45 (dd, J=11.15, 4.50 Hz, 1H), 3.35 (d, J=6.16 Hz, 1H), 2.76-2.68 (m, 1H), 2.51-2.44 (dd, J=13.05, 5.86 Hz, 1H), 2.39-2.32 (dd, J=13.05, 7.48 Hz, 1H). $^{13}$C NMR (75 MHz, CD$_3$OD) δ 144.56, 130.15, 129.02, 128.02, 69.87, 64.93, 63.21, 53.78, 33.25. HPLC-MS: Elution with 30% CH$_3$CN in H$_2$O (gradient 1.5% min$^{-1}$), exhibited a single peak at 3.92 min. ESI-MS m/z [ES+] calcd for C$_{17}$H$_{21}$NO$_2$S [M+H]$^+$304.16; found 304.13.

EXAMPLE 7

Synthesis of Compound 2.3 (STLC-NCA)

Scheme G

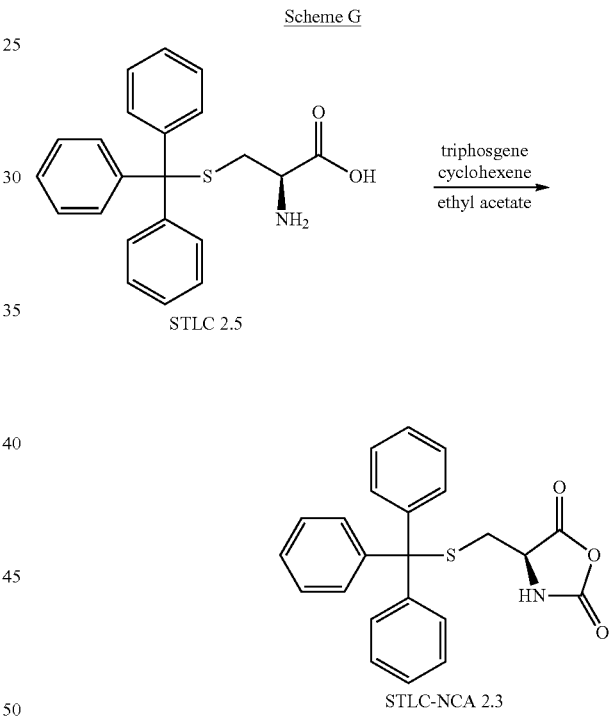

Triphosgene (0.312 g, 1.05 mmol) was added to a mixture of compound 2.5 (STLC) (0.181 g, 0.5 mmol) and cyclohexene (0.410 g, 5 mmol) in ethyl acetate (5 mL) at 0° C. as is illustrated in Scheme G. The reaction mixture was allowed to reflux for 3 h. The volatiles were removed in vacuo to obtain the crude residue as pale yellow solid. The crude material was dissolved in methylene chloride (20 mL), washed with water (35 mL), organic layer was dried over anhydrous sodium sulfate, and the solvents were evaporated under reduced pressure to provide the product as colorless solid (0.165 g, 85%). IR (KBr, cm$^{-1}$): 3250, 2956, 1779, 1634, 1212. $^1$H NMR (300 MHz, CDCl$_3$) δ 7.43-7.39 (m, 5H), 7.32-7.19 (m, 10H), 5.79 (s, 1H), 3.53-3.49 (m 1H), 2.78-2.63 (m, 2H); $^{13}$C NMR (75 MHz, CDCl$_3$) δ 167.76, 151.00, 143.69, 129.33, 128.29, 127.26, 67.76, 56.46, 33.24.

EXAMPLE 8

Synthesis of Cysteine Reagent Compound 2.4 (MSTLC-NCA)

Scheme H

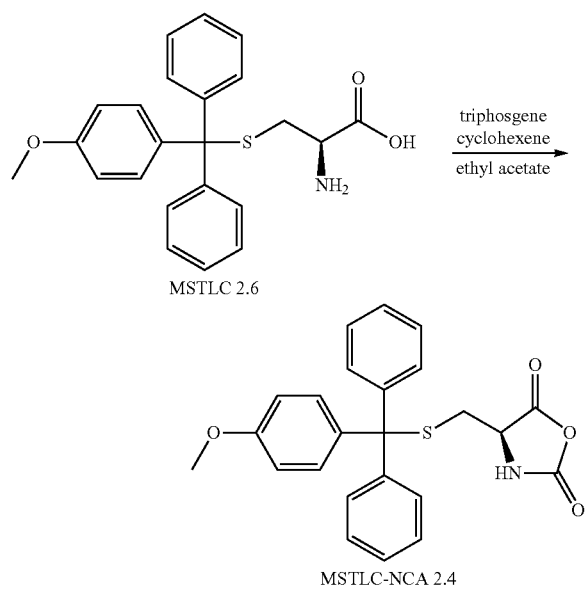

Triphosgene (about 0.932 g, 3.15 mmol) was added to a mixture of compound 2.6 (MSTLC) (about 0.589 g, 1.5 mmol) and cyclohexene (about 1.23 g, 15 mmol) in ethyl acetate (about 10 mL) at approximately 0° C. as is illustrated in Scheme H. The reaction was heated at about 85° C. for approximately 3 hours. The volatiles were removed in vacuo and the crude material was dissolved in methylene chloride (about 20 mL) and washed with water (about 35 mL). The organic layer was dried over anhydrous sodium sulfate and concentrated under reduced pressure to obtain the product as a colorless solid (about 0.525 g, 84%). $^1$H (300 MHz, CDCl$_3$): δ 7.53-7.08 (m, 12H), 6.93-6.73 (m, 2H), 5.15 (s, 1H), 3.80 (s, 3H), 3.58-3.51 (dd, J=8.51, 3.96 Hz, 1H), 2.87-2.68 (m, 2H). $^{13}$C NMR (300 MHz, CDCl$_3$): δ 167.85, 158.43, 151.17, 144.00, 135.65, 130.58, 129.22, 128.24, 127.15, 113.50, 67.28, 56.53, 55.26, 33.27.

EXAMPLE 9

Synthesis of Cysteine Derivative Compound 3.4 (S3PTLC)

Scheme I

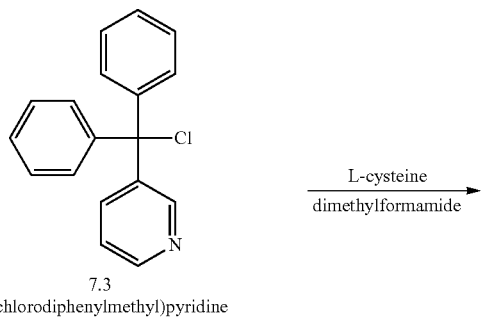

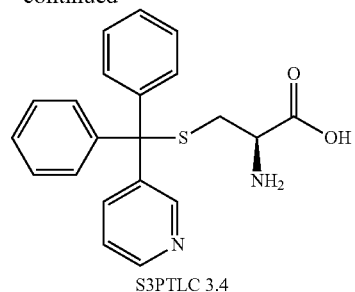

A mixture of compound 7.3 (3-(chlorodiphenylmethyl) pyridine) and compound 2.2 (L-cysteine) in dry DMF (3 mL) was allowed to stir under argon at room temperature for 48 h. Aqueous sodium acetate solution was added to the reaction mixture and the white precipitate was filtered, washed with water (10 mL), and dried in vacuo. The residue was purified by silica gel column chromatography using methanol/methylene chloride (15:85) to provide the product as white solid (0.012 g, 6%). IR (KBr, cm$^{-1}$): 3433, 2923, 1627, 1383, 1108. $^1$H (300 MHz, CD$_3$OD) δ 8.22 (d, J=1.6 Hz, 1H), 7.40 (dd, J=6.50, 2.1 Hz, 1H), 7.31-7.09 (m, 12H), 3.92 (dd, J=7.6, 3.06 Hz, 1H), 3.77 (dd, J=14.97, 3.09 Hz, 1H), 3.48 (dd, J=15.15, 7.7 Hz, 1H); $^{13}$C NMR (75 MHz, CD$_3$OD) δ: 155.40, 149.62, 142.69, 137.95, 137.08, 128.90, 128.23, 126.42, 122.30, 55.18, 53.52, 32.09. HPLC-MS: Elution with 60-90% CH$_3$CN in H$_2$O (gradient 1.5% min$^{-1}$), exhibited a single peak at 3.92 min. ESI-MS m/z [ES+] calcd for C$_{21}$H$_{20}$N$_2$O$_2$S [M+H]$^+$365.33; found 365.12.

EXAMPLE 10

Synthesis of Cysteine Derivative Compound 3.5 (STPY)

Scheme J

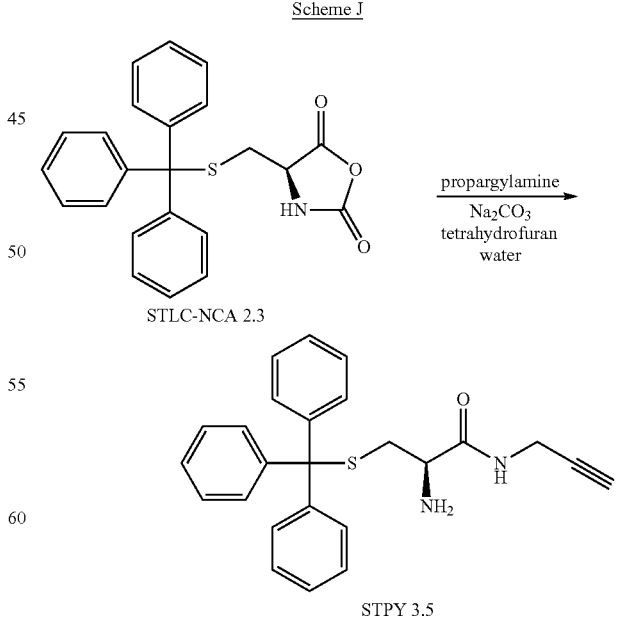

To a mixture of sodium carbonate (0.423 g, 4 mmol) and propargylamine (0.55 g, 10 mmol) in water (5 mL) was added a solution of compound 2.3 STLC-NCA (0.389 g, 1 mmol) in THF (3 mL) at 0° C. over 15 min and allowed to stir at room temperature for 24 h as is illustrated in Scheme J. The reaction mixture was concentrated, dissolved in CH$_2$Cl$_2$ (25 mL), filtered through celite, the organic layer was dried over anhydrous sodium sulfate, and then evaporated under reduced pressure to obtain a colorless oil. The residue was purified by silica gel column chromatography using methanol/methylene chloride (5:95) as eluent to isolate the product compound 3.5 STPY as a colorless solid (0.338 g, 84%). IR (KBr, cm$^{-1}$): 3281, 2103, 1657, 1592, 1488. $^1$H NMR (300 MHz, CDCl$_3$) δ 7.45-7.43 (m, 5H), 7.31-7.18 (m, 10H), 4.03-3.88 (m, 2H), 3.03-2.93 (m 1H), 2.74 (dd, J=12.76, 3.81 Hz, 1H), 2.54 (dd, J=12.77, 8.66 Hz, 1H), 2.18 (t, J=2.50 Hz, 1H), 1.38 (s, 3H); $^{13}$C NMR (75 MHz, CDCl$_3$) δ 172.57, 144.49, 129.54, 127.93, 126.77, 79.41, 71.40, 67.00, 53.88, 37.15, 28.78 HPLC-MS: Elution with 20-80% CH$_3$CN in H$_2$O (gradient 1.5% min$^{-1}$), exhibited a single peak at 4.42 min. ESI-MS m/z [ES+] calcd for C$_{25}$H$_{24}$N$_2$OSNa [M+Na]$^+$423.36; found 423.15.

EXAMPLE 11

Synthesis of Cysteine Derivative Compound 4.0 (MSTPY)

Scheme K

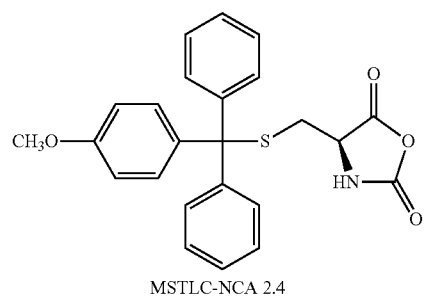

MSTLC-NCA 2.4

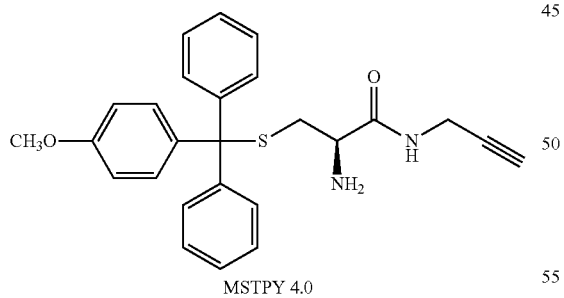

MSTPY 4.0

To a mixture of sodium carbonate (about 0.635 g, 6 mmol) and propargylamine (about 0.550 g, 10 mmol) in water/THF (about 2:1 mL) was added a solution of compound 2.4 (MSTLC-NCA) (about 0.419 g, 1 mmol) in THF (about 3 mL) at approximately 0° C. over about 30 min and allowed to stir at room temperature for about 1 hour as is illustrated in Scheme K. The reaction mixture was diluted with water and extracted with CH$_2$Cl$_2$ (about 20 mL). The product was dried over Na$_2$SO$_4$ and volatiles were removed by rotary evaporation. The crude product was purified by silica gel column chromatography using MeOH/CH$_2$Cl$_2$(2:98) as eluent to isolate the product 4.0 MSTPY as a colorless solid (about 0.340 g, 80%). FT-IR (KBr): 3546, 2360, 1656, 1458, 1250 cm$^{-1}$. $^1$H (300 MHz, CDCl$_3$): δ 7.45-7.20 (m, 12H), 6.85-6.75 (m, 2H), 4.25-3.26 (m, 2H), 3.78 (s, 3H), 3.07-3.00 (dd, J=8.80, 3.81 Hz, 1H), 2.79-2.70 (dd, J=12.76, 3.81 Hz, 1H), 2.60-2.49 (dd, J=12.76, 8.80 Hz, 1H), 2.26-2.24 (t, J=2.50 Hz, 1H), 1.48-1.27 (s, 2H). $^{13}$C NMR (300 MHz, CDCl$_3$): δ 172.69, 158.19, 144.86, 136.62, 130.78, 129.51, 127.98, 126.78, 113.25, 79.48, 61.46, 66.57, 55.26, 53.96, 37.27, 28.87. HPLC-MS (ES$^+$) m/z: 453.29 [(M+Na)$^+$, C$_{26}$H$_{26}$N$_2$O$_2$SNa requires 453.15.

EXAMPLE 12

Synthesis of Cysteine Derivative Compound 3.6 (ASTCC)

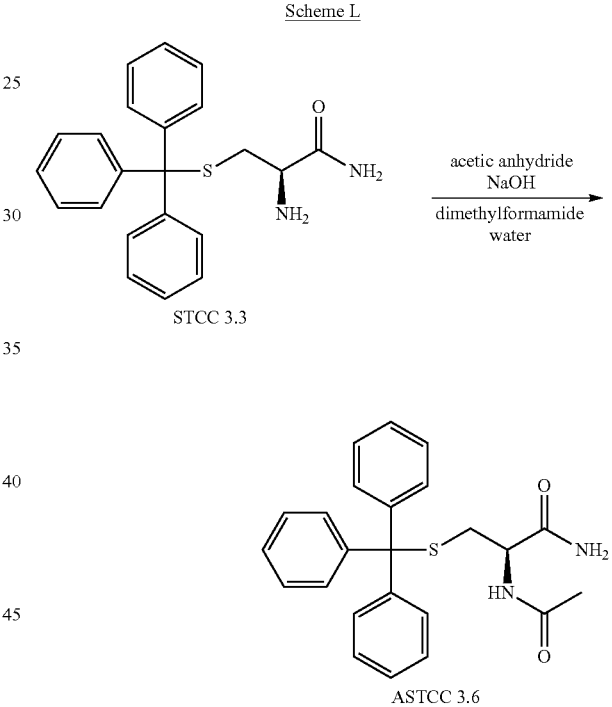

Acetic anhydride (0.102 g, 0.92 mmol) was added to the mixture of compound 3.3 (STCC) (0.022 g, 0.061 mmol) and sodium hydroxide (0.0048 g, 0.12 mmol) in a mixture of DMF (0.25 mL) and water (0.5 mL) as is illustrated in Scheme L. The reaction was allowed to stir at rt for 1 h. The reaction mixture was diluted with water (20 mL), the product was extracted with ethyl acetate (3×25 mL), dried over anhydrous sodium sulfate, volatiles were evaporated under reduced pressure to obtain compound 3.6 ASTCC as a colorless solid (0.023 g, 94%). IR (KBr, cm$^{-1}$): 3392, 3294, 1656, 1595, 1489. $^1$H NMR (300 MHz, CDCl$_3$) δ 7.45-7.42 (m, 5H), 7.32-7.22 (m, 10H), 6.04 (s, 1H), 5.85 (d, J=7.42 Hz, 1H), 5.45 (bs, 1H), 4.19-4.12 (m, 1H), 2.74 (dd, J=13.08, 6.83 Hz, 1H), 2.56 (dd, J=13.08, 5.66 Hz, 1H), 1.89 (s, 3H); $^{13}$C NMR (75 MHz, CDCl$_3$) δ 172.19, 170.22, 144.33, 129.53, 128.07, 127.90, 126.92, 51.76, 33.04, 23.08. HPLC-MS: Elution with 20-80% CH$_3$CN in H$_2$O (gradient 1.5% min$^{-1}$), exhibited a single peak at 8.03 min. ESI-MS m/z [ES+] calcd for $C_{24}H_{26}N_2O_2S$ [M+H]$^+$ 405.22; found 405.16]

EXAMPLE 13

Synthesis of Cysteine Derivative Compound 3.7 (DPALC)

Scheme M

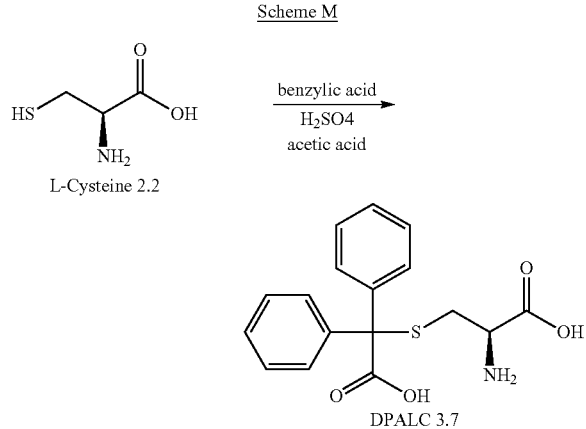

Concentrated sulfuric acid (0.6 mL) was added dropwise to benzilic acid (0.3 g, 1.315 mmol) and compound 2.2 (L-cysteine) in glacial acetic acid (3 mL) at 40° C. and allowed to stir for 3 h as is illustrated in Scheme M. To the reaction mixture, was added ice cold water (10 mL) and allowed to stir for 1 h at room temperature. The white precipitate obtained was filtered, washed with cold water (25 mL) and hexanes (5 mL) and dried in vacuo to provide the pure product as white solid (0.4 g, 92%). IR (KBr, cm$^{-1}$): 2921, 1717, 1489, 1110, 699. $^1$H (300 MHz, CD$_3$OD) δ 7.45-7.28 (m, 10H), 3.72-3.68 (dd, J=4.5 Hz, 1H), 2.90-2.74 (m, 2H); $^{13}$C NMR (75 MHz, CD$_3$OD) δ 141.47, 141.19, 139.36, 138.33, 129.98, 129.36, 128.28, 127.40, 126.85, 81.12, 65.42, 34.57. HPLC-MS: Elution with 60-90% CH$_3$CN in H$_2$O (gradient 1.5% min$^{-1}$), exhibited a single peak at 3.92 min. ESI-MS m/z [ES−] calcd for $C_{17}H_{17}NO_4S$ [M$^-$] 329.98; found 329.09.

EXAMPLE 14

Synthesis of Cysteine Derivative Compound 3.8 (STCB)

Scheme N

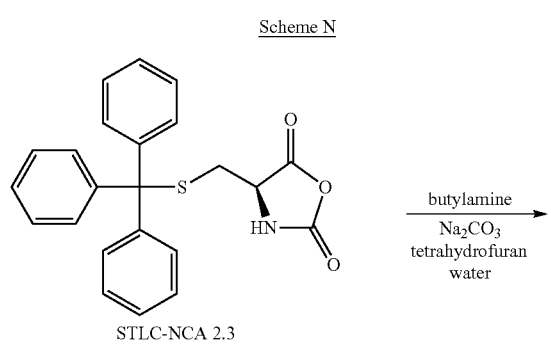

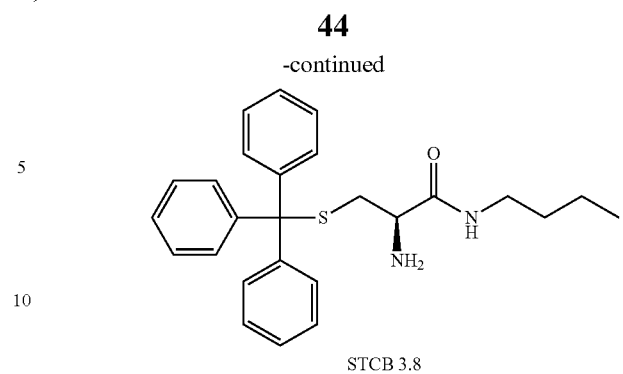

STCB 3.8

To a mixture of sodium carbonate (0.105 g, 1 mmol) and butylamine (0.183 g, 2.5 mmol) in water (5 mL) at 0° C. was slowly added a solution of compound 2.3 (STLC-NCA) (0.097 g, 0.25 mmol) in tetrahydrofuran (1 mL) over 15 min, and then allowed to stir at room temperature for 24 h as is illustrated in Scheme N. The reaction mixture was concentrated, dissolved in CH$_2$Cl$_2$ (25 mL), filtered through celite, the organic layer was dried over anhydrous sodium sulfate, and then concentrated under reduced pressure to obtain a colorless oil. The crude oil was purified by silica gel column chromatography using methanol/methylene chloride (5:95) as eluent to isolate the product compound 3.8 STCB as colorless oil (0.093 g, 90%). IR (KBr, cm$^{-1}$): 3052, 2924, 1650, 1593, 1487. $^1$H NMR (300 MHz, CDCl$_3$) δ 7.44-7.42 (m, 6H), 7.29-7.17 (m, 9H), 6.97 (bs, 1H), 3.15 (q, J=12.91, 6.75 Hz, 2H), 3.01 (dd, J=8.36, 3.66 Hz, 1H), 2.72 (dd, J=2.76, 3.96 Hz, 1H), 2.53 (dd, J=12.77, 8.66 Hz, 1H), 1.46-1.25 (m, 6H), 0.88 (t, J=7.19 Hz, 3H); $^{13}$C NMR (75 MHz, CDCl$_3$) δ 172.66, 144.54, 129.53, 127.87, 126.69, 66.89, 53.97, 38.73, 37.41, 31.47, 19.97, 13.66. HPLC-MS: Elution with 20-80% CH$_3$CN in H$_2$O (gradient 1.5% min$^{-1}$), exhibited a single peak at 4.35 min. ESI-MS m/z [ES+] calcd for $C_{26}H_{30}N_2OSNa$ [M+Na]$^+$ 441.36; found 441.19.

EXAMPLE 15

Synthesis of Cysteine Derivative Compound 3.9 (MASTC)

Scheme O

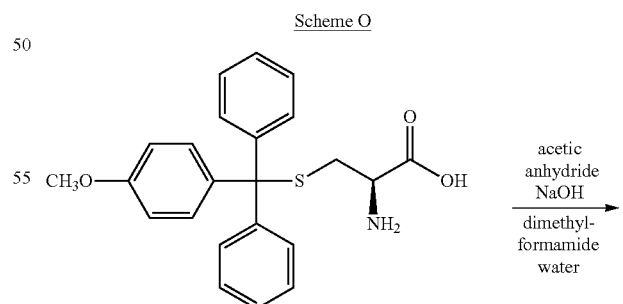

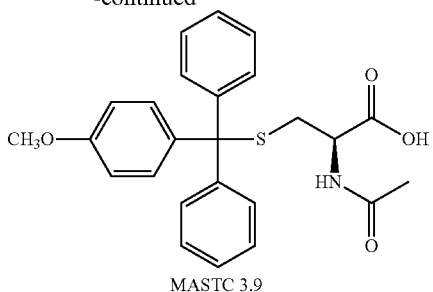

MASTC 3.9

Acetic anhydride (0.153 g, 1.5 mmol) was added to a mixture of compound 2.6 MSTLC (0.393 g, 1 mmol) and sodium carbonate (0.210 g, 2 mmol) in DMF (1 mL) and water (0.5 mL) as is illustrated in Scheme O. The reaction was allowed to stir at rt for 1 h. The reaction mixture was diluted with water (20 mL), the product was extracted with ethyl acetate (3×25 mL), dried over anhydrous sodium sulfate, volatiles were evaporated under reduced pressure to obtain compound 3.9 MASTC as a colorless solid (0.410 g, 96%). IR (KBr, cm$^{-1}$): 3387, 3293, 1651, 1591, 1479. $^1$H NMR (300 MHz, CDCl$_3$) δ 7.37-7.17 (m, 12H), 6.79 (d, J=8.7 Hz, 2H), 6.13 (d, J=7.61 Hz, 1H), 4.53-4.48 (m, 1H), 3.76 (s, 3H), 2.75 (dd, J=12.69, 5.69 Hz, 1H), 2.67 (dd, J=12.69, 4.68 Hz, 1H), 1.89 (s, 3H).

EXAMPLE 16

Synthesis of cysteine derivative compound 4.1 (MSTDC)

Scheme P

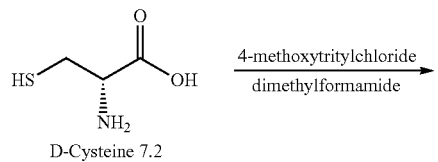

D-Cysteine 7.2

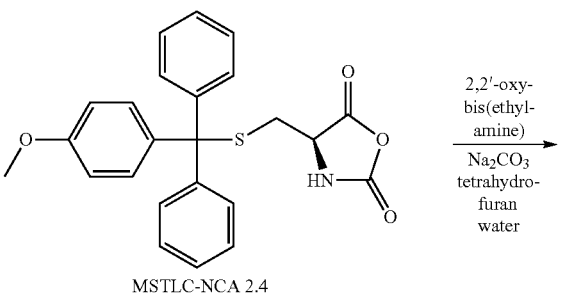

MSTDC 4.1

A mixture of 4-methoxy tritylchloride (0.152 g, 0.49 mmol), compound 7.2 D-cysteine (0.050 g, 0.41 mmol) in dry DMF (2 mL) was allowed to stir under argon at room temperature for 48 h as is illustrated in Scheme P. Aqueous sodium acetate solution was added to the reaction mixture and the white precipitate was filtered, washed with water (10 mL), and dried in vacuo. The residue was purified by silica gel column chromatography using methanol/methylene chloride (20:80) to provide the product compound 4.1 MSTDC as white solid (0.150 g, 92%).

EXAMPLE 17

Synthesis of Cysteine Derivative Compound 4.2 (MSTLCB)

Scheme Q

MSTLC-NCA 2.4

MSTLCB 4.2

To a mixture of sodium carbonate (0.210 g, 2 mmol) and 2,2'-oxybis(ethylamine) (0.520 g, 5 mmol) in THF/H$_2$O (3:3 mL), was added a solution of compound 2.4 (MSTLC-NCA) (0.210 g, 0.5 mmol) in THF (6 mL) at 0° C. over 30 min and allowed to stir at room temperature for 1 h as is illustrated in Scheme Q. The reaction mixture was concentrated and water (25 mL) was added. The resulting precipitate was filtered and dried. The crude solid was purified by silica gel column chromatography using methanol/methylene chloride (20:80) to isolate the product compound 4.2 MSTLCB (0.041 g, 55%). IR (KBr, cm$^{-1}$): 3391, 2954, 1658, 1384, 1250. $^1$H NMR (300 MHz, CDCl$_3$) δ 7.45-7.17 (m, 12H), 6.85-6.75 (m, 2H), 3.78 (s, 3H), 3.55-3.30 (m, 6H), 3.10-3.00 (dd, J=8.37, 3.97 Hz, 1H), 2.85-2.78 (t, J=5.06 Hz, 2H), 2.76-2.67 (dd, J=4.11, 4.11 (12.62, 4.11) Hz, 1H), 2.60-2.50 (dd, J=12.62, 8.36 Hz, 1H), 1.76 (s, 2H); $^{13}$C NMR (75 MHz, CDCl$_3$) δ 172.97, 158.11, 144.86, 136.61, 130.73, 129.46, 127.89, 126.68, 113.16, 72.69, 69.48, 66.41, 55.19, 54.02, 41.53, 38.89, 37.47. HPLC-MS: Elution with 20-80% CH$_3$CN in H$_2$O (gradient 1.5% min$^{-1}$), exhibited a single peak at 8.32 min. ESI-MS m/z [ES+] calcd for $C_{27}H_{34}N_3O_3S$ [M+H]$^+$ 480.17; found 480.22.

EXAMPLE 18

Synthesis of Compound 7.4 (MSTLC-succinimide ester)

Scheme R

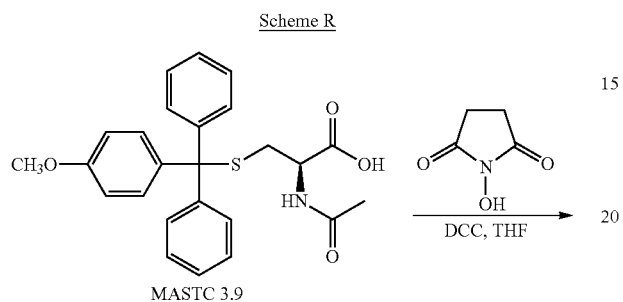

MASTC 3.9

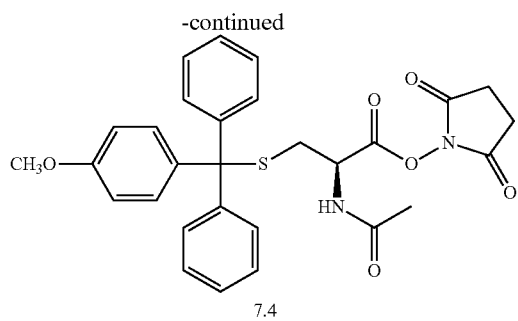

7.4

To a mixture of compound 3.9 (MASTC) (N-acetylated MSTLC) (about 0.215 g, 0.49 mmol) and N-hydroxy succinimide (about 0.056 g, 0.49 mmol) in THF (about 0.98 mL) was added dicyclohexyl carbodimide (about 0.100 g, 0.49 mmol) at approximately 0° C. and allowed to stir for about 4 hours at room temperature as is illustrated in Scheme R. The reaction mixture was filtered through a funnel and washed with cold THF (about 2 mL), the filtrate was concentrated and dried under vacuum to obtain compound 7.4 as a colorless solid (about 0.234 g, 90%). FT-IR (KBr): 3328, 2931, 1816, 1784, 1739, 1031 cm$^{-1}$. $^1$H (300 MHz, CDCl$_3$): δ 7.56-7.13 (m, 12H), 6.93-6.75 (m, 2H), 5.72-5.64 (d, J=7.92 Hz, 1H), 4.78-4.67 (m, 1H), 3.79 (s, 3H), 2.76-2.65 (m, 1H), 1.92 (s, 3H). $^{13}$C NMR (300 MHz, CDCl$_3$): δ 172.65, 172.45, 171.15, 168.58, 166.30, 158.15, 144.53, 144.30, 136.24, 135.97, 130.67, 129.31, 127.97, 125.81, 113.24, 66.55, 55.20, 51.37, 49.56, 33.43, 33.25, 25.48, 25.30, 24.72, 22.77, 22.59. HPLC-MS (ES$^+$) m/z: 555.42 [(M+Na)$^+$, $C_{29}H_{28}N_2O_6$SNa requires 555.15.

EXAMPLE 19

Synthesis of Compound 7.5 (N-acetyl-MSTLC-bisamine)

Scheme S

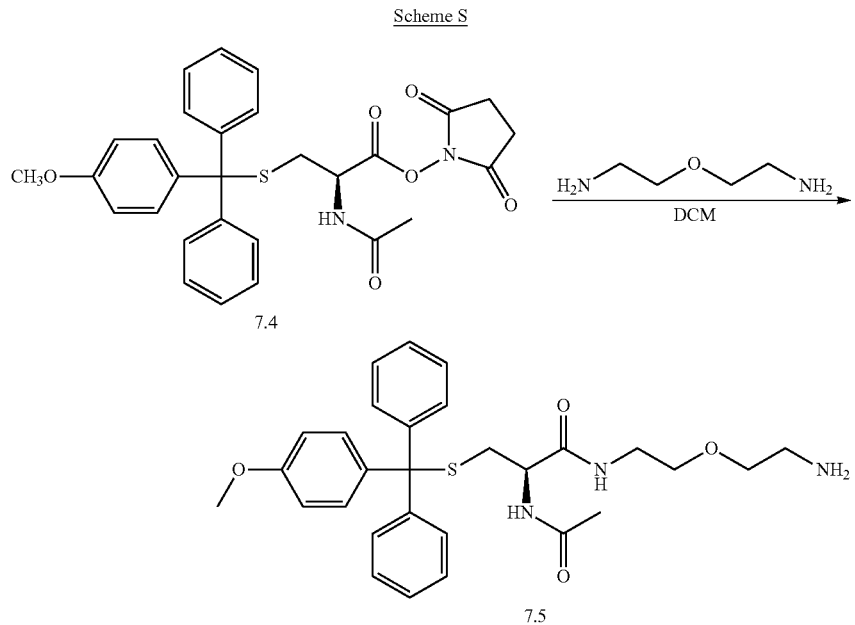

Compound 7.4 (N-acetyl-MSTLC-succinimide ester) (about 0.133 g, 0.25 mmol) in methylene chloride (approximately 5 mL) was slowly added to 2,2'-oxybis (ethylamine) (about 0.260 g, 2.5 mmol) in methylene chloride (about 5 mL) at approximately 0° C. for about 1 hour as is illustrated in Scheme S. The reaction mixture was filtered and the filtrate was concentrated under vacuum. The crude product was purified by silica gel column chromatography using MeOH/CH$_2$Cl$_2$(5:95) to obtain the product compound 7.5 as a colorless solid (about 69 mg, 53%). FT-IR (KBr): 3435, 2923, 1634, 1251, 1116 cm$^{-1}$. $^1$H (300 MHz, CDCl$_3$): 7.42-7.19 (m, 12H), 6.90-6.80 (m, 2H), 4.27-4.20 (t, J=7.33 Hz, 1H), 3.79 (s, 3H), 3.54-3.43 (m, 4H), 3.40-3.30 (m, 2H), 2.81-2.73 (t, J=4.99 Hz, 2H), 2.63-2.45 (m, 2H), 1.94 (s, 3H). $^{13}$C NMR (300 MHz, CDCl$_3$): δ 171.52, 171.08, 158.45, 144.90, 136.34, 130.60, 129.22, 127.60, 126.48, 112.87, 71.43, 68.88, 66.19, 54.37, 52.63, 40.65, 39.06, 33.52, 21.10. HPLC-MS (ES$^+$) m/z: 522.48 (MH$^+$, $C_{29}H_{36}N_3O_4S$ requires 521.23).

EXAMPLE 20

Development of Solid-Phase Affinity Probes for EG5

Replacement of the carboxylic acid with a variety of carboxamide groups resulted in no reduction in inhibitory activity, and in the case of the alcohol derivative compound 1.0 (MSTCO), there was a significant enhancement of activity without a loss of motor specificity Table 3. As a first estimation of whether the plasticity of the molecule at this position could retain activity with more extensive functional groups, a methoxy-STLC derivative (compound 4.2 (MSTLCB) was linked to solid-phase sepharose beads via a short linker compound 7.6, (FIG. 1, Panel A). As a negative control, the N-acyl derivative compound 7.5 (MASTC) was linked to the solid-phase sepharose beads compound 7.7 (FIG. 1, Panel A). To determine whether these solid-phase analogs could bind Eg5, compounds 7.6 and 7.7 were incubated with *Xenopus leavis* oocyte cell-free extracts separated from the unbound fraction, washed, resolved by SDS-PAGE and Western blotting and probed for the presence of Eg5 (FIG. 1). Whereas Eg5 was detected in the unbound fractions of both compounds 7.6 and 7.7 (FIG. 1, Lanes 2 and 4), Eg5 was only found in the bound fraction eluted from compound 7.6 (FIG. 1, Lanes 3 and 5). Together, these results suggested that more extensive derivitization of the carboxyl group can be performed without sacrificing binding affinity, and underscored the requirement for the amino group for both binding and inhibitory activity.

EXAMPLE 21

Synthesis of Solid-Phase Affinity Probes for Eg5 Cysteine Derivative Compound 7.6 (MSTLCB-Sepharose)

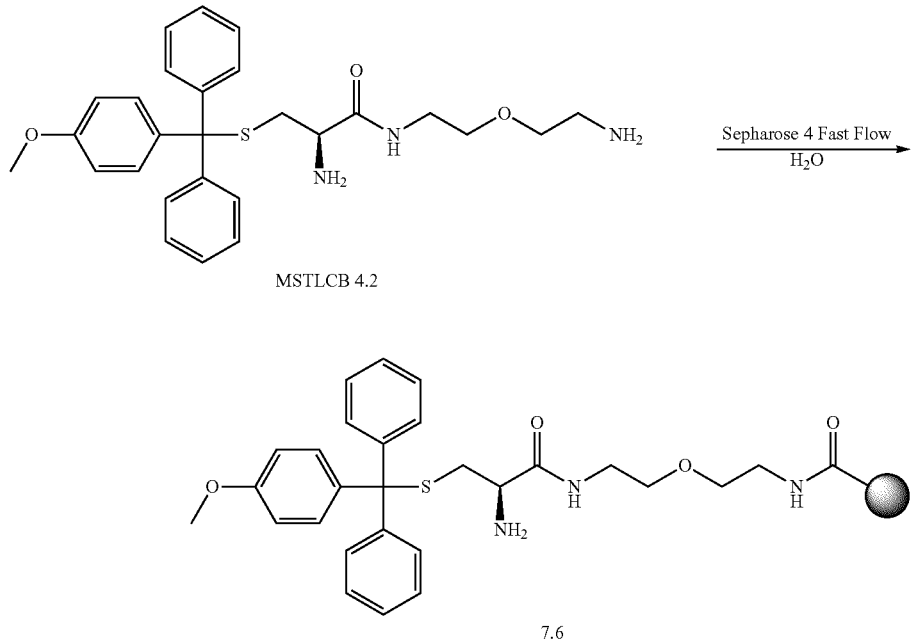

Sepharose 4 fast flow (about 1.5 mL) was washed with HCl (about 20 mL, 1 mM) at approximately 0° C. and taken in deionized water (about 3 mL) as is illustrated in Scheme T. The gel was added to MSTLC-Bisamine (about 16 mg) in water (about 1 mL) at approximately 0° C. and the pH was brought to about 7.1 by the addition of triethylamine and about 1 mM HCl. The reaction mixture was allowed to shake overnight at room temperature. The gel was filtered and washed with water (about 20 mL). The gel was then washed with ethanolamine (about 6 mL, 1 mM, pH 8), tris buffer (about 6 mL, 50 mM, pH 8), and acetic acid buffer (about 5 mL, 70 mM, pH 4). The tris buffer and acetic acid washings were repeated and the reaction mixture was washed with ultrapure water (about 25 mL). The mixture was stored in approximately 6 mL of $H_2O$/EtOH (8:2). FT-IR (KBr): 2921, 1639, 1257, 1079, 928 cm$^{-1}$. (Emmanuel Klein, et al., (2007) *New Chemical Tools for Investigating Human Mitotic Kinesin Eg5*. Bioorganic & Medicinal Chemistry 15, 6474-6488).

EXAMPLE 22

Synthesis of Solid-Phase Affinity Probes for Eg5 Cysteine Derivative Compound 7.7 (MASTC-Sepharose)

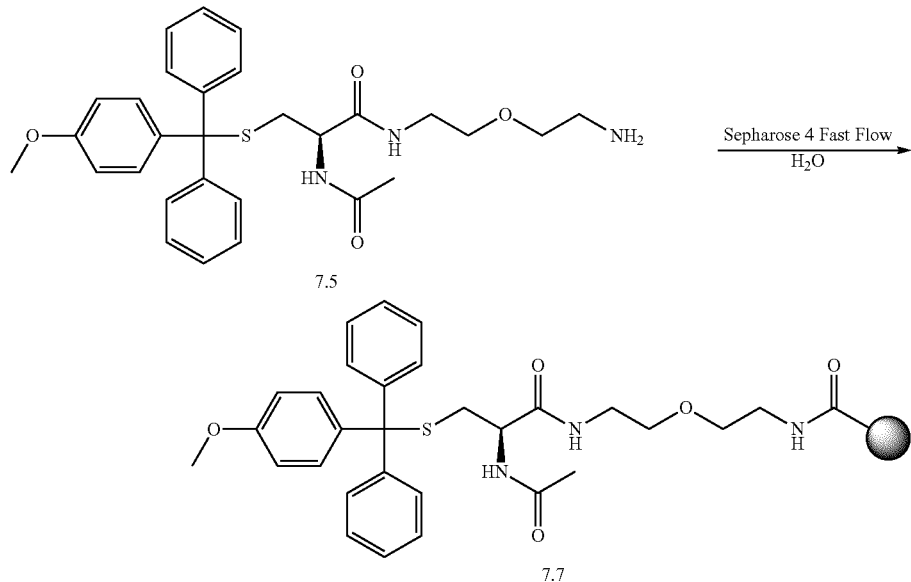

Scheme U

Sepharose 4 fast flow (about 1.5 mL) was washed with HCl (about 20 mL, 1 mM) at approximately 0° C. and taken in de-ionized water (about 3 mL) as is illustrated in Scheme U. The gel was added to compound 7.5 (N-acetyl-MSTLC-bisamine) in deionized water (about 1 mL). The pH was brought to about 7.12 by the addition of triethylamine and about 1 mM HCl. The reaction mixture was allowed to shake overnight at room temperature. The gel was filtered and washed with of water (about 20 mL). The gel was then washed with ethanol amine (about 6 mL, 1 mM, pH 8), tris buffer (about 6 mL, 50 mM, pH 8), and acetic acid buffer (about 5 mL, 70 mM, pH 4). The tris buffer and acetic acid washings were repeated and finally the gel was washed with of ultra-pure water (about 25 mL). The mixture was stored in a mixture of about 6 mL of water/ethanol (8:2).

EXAMPLE 23

A compound of the formula I having the structure of compound 1.0 (MSTCO, NSC 747880) was screened through the NCI Drug Therapeutics program for its anti-proliferative activity against 60 cancer cell lines. MSTCO exhibited promising activity at a single concentration, and was advanced to a secondary dose-response study, where efficacy against leukemia and breast cancer cell lines was established.

Referring to Table 2, Growth inhibitory activities for Monastrol (NSC 716782), compound 2.5 STLC(NSC 83265) and compound 1.0 MSTCO(NSC 747880) are illustrated. After an initial screen at a single dose (10 µM), MSTCO was screened over a range of doses, and the resulting $GI_{50}$ values are shown in Table 2 along with the data previously determined for Monastrol and STLC. Although MSTCO values ranged from 20 nM to 3 µM the average GI50 was 360 nM, representing an average 143- and 35-fold increases in activity over Monastrol and STLC, respectively. However, there were instances such as the melanoma cell line M14 where MSTCO displayed a 1200-fold increase in activity over monastrol and a 20-fold increase over the parent compound STLC.

TABLE 2

| Cell Line | | Monastrol | STLC | MSTCO |
|---|---|---|---|---|
| Leukemia | CCRF-CEM | 31.6 | 1.58 | 0.1 |
| Leukemia | HL-60(TB) | 25.1 | 2.51 | 0.19 |
| Leukemia | K-562 | 31.6 | 1.58 | 0.06 |
| Leukemia | MOLT-4 | 31.6 | 7.94 | 0.28 |
| Leukemia | RPMI-8226 | 31.6 | 3.16 | 0.03 |
| Leukemia | SR | 31.6 | 6.31 | 0.01 |
| Non-Small Cell Lung | A549/ATCC | 50.1 | 5.01 | 0.33 |
| Non-Small Cell Lung | EKVX | 63.1 | 3.16 | 0.51 |
| Non-Small Cell Lung | HOP-62 | 63.1 | 19.9 | 0.51 |
| Non-Small Cell Lung | NCI-H226 | 50.1 | 100 | 2.75 |
| Non-Small Cell Lung | NCI-H23 | 63.1 | 2.51 | 0.26 |
| Non-Small Cell Lung | NCI-H322M | 39.8 | 1.26 | 0.11 |
| Non-Small Cell Lung | NCI-H522 | 31.6 | 0.5 | 0.22 |
| Colon | COLO 205 | 31.6 | 3.16 | 0.08 |
| Colon | HCC-2998 | 39.8 | 2.51 | 0.05 |
| Colon | HCT-116 | 31.6 | 0.5 | 0.03 |
| Colon | HCT-15 | 39.8 | 2.51 | 0.21 |
| Colon | HT29 | 79.4 | 3.98 | 0.34 |
| Colon | KM12 | 31.6 | 5.01 | 0.22 |
| Colon | SW-620 | 39.8 | 1.58 | 0.07 |
| Central Nervous System | SF-268 | 63.1 | 3.98 | 0.11 |
| Central Nervous System | SF-295 | 31.6 | 0.5 | 0.28 |
| Central Nervous System | SF-539 | 50.1 | 0.79 | 0.26 |
| Central Nervous System | SNB-19 | 79.4 | 2.51 | 0.25 |
| Central Nervous System | SNB-75 | 39.8 | 1.99 | 0.26 |
| Central Nervous System | U251 | 31.6 | 1 | 0.19 |
| Melanoma | LOX IMVI | 79.4 | 6.31 | 0.49 |
| Melanoma | MALME-3M | 63.1 | 1.26 | 0.36 |
| Melanoma | M14 | 25.1 | 0.398 | 0.02 |

TABLE 2-continued

| Cell Line | | Monastrol | STLC | MSTCO |
|---|---|---|---|---|
| Melanoma | SK-MEL-2 | 31.6 | 1.5 | 0.24 |
| Melanoma | SK-MEL-28 | 79.4 | 12.6 | 0.62 |
| Melanoma | SK-MEL-5 | 39.8 | 0.63 | 0.06 |
| Melanoma | UACC-257 | 63.1 | 1.26 | 0.54 |
| Melanoma | UACC-62 | 39.8 | 1.99 | 0.25 |
| Ovarian | IGROV1 | 50.1 | 3.98 | 0.26 |
| Ovarian | OVCAR-3 | 50.1 | 2.51 | 0.2 |
| Ovarian | OVCAR-4 | 63.1 | 12.6 | 1.62 |
| Ovarian | OVCAR-5 | 79.4 | 100 | 0.39 |
| Ovarian | OVCAR-8 | 63.1 | 1.99 | 0.42 |
| Ovarian | SK-OV-3 | 63.1 | 100 | 0.08 |
| Renal | 786-0 | 63.1 | 1.26 | 0.44 |
| Renal | ACHN | 79.4 | 19.9 | 0.49 |
| Renal | CAKI-1 | 63.1 | 15.8 | 0.45 |
| Renal | SN12C | 39.8 | 3.16 | 0.32 |
| Renal | TK-10 | 100 | 6.31 | 0.46 |
| Renal | UO-31 | 100 | 100 | 1.1 |

MSTCO was screened against the NCI60 tumor panel. Cell lines shown above represent lines common to all three screens, and growth inhibition is expressed as the concentration of drug (μM) that achieved 50% growth inhibition.

EXAMPLE 24

In Vitro and In Vivo Effects of Eg5 Inhibitors of Eg5 Activity

Biochemical- and cell-based assays were used to evaluate the inhibitory activities of the STLC analogs. Using a commercially available assay from Cytoskeleton, Inc, analogs were assayed for their ability to block the microtubule-activated ATPase activity of recombinant human EG5 motor domain. In parallel, HeLa cells were treated for four hours with a range of concentrations, and then fixed, stained for microtubules, and mitotic cells were scored for spindle bipolarity. Results of these assays are summarized in Table 3. Referring now to Table 3, $IC_{50}$ values for inhibition of microtubule activate Eg5 ATPase activity and bipolar spindle formation in HeLa cervical adenocarcinoma cells is illustrated.

Analogs that contained modifications to the trityl group (compound 2.9 (SBHC), compound 2.7 (SFMC), compound 3.0 (SFC), compound 3.4 (S3PTLC)) had no measurable activity in either assay, as did amino derivatives (compound 3.1 (ASTC), compound 3.6 (ASTCC), compound 3.9 (MASTC)). However, derivatives of the carboxylic acid retained- or displayed enhanced in inhibitory activity in both the biochemical- and cell-based assays. MSTCO was the best performing analog. Referring to table 3, $IC_{50}$ values for inhibition of microtubule-activated Eg5 ATPase activity and bipolar spindle formation in HeLa cervical adenocarcinoma cells treated with analog for 4 hours and scored for bipolar vs monopolar spindle formation is illustrated.

TABLE 3

| Compound | Eg5 ATPase $IC_{50}$ (μM) | Bipolar spindle formation $IC_{50}$ (μM) |
|---|---|---|
| 2.5 STLC | 0.58 | 0.66 |
| 2.9 SBHC | >100 | >100 |
| 2.7 SFMC | >100 | >100 |
| 3.0 SFC | >100 | >100 |
| 3.4 S3PTLC | >100 | >100 |
| 2.8 OTC | 0.76 | 0.85 |
| 3.1 ASTC | >100 | >100 |
| 3.6 ASTCC | >100 | >100 |

TABLE 3-continued

| Compound | Eg5 ATPase $IC_{50}$ (μM) | Bipolar spindle formation $IC_{50}$ (μM) |
|---|---|---|
| 3.9 MASTC | >100 | >100 |
| 3.2 STCM | 0.51 | 0.92 |
| 3.3 STCC | 0.54 | 0.67 |
| 3.8 STCB | 0.56 | 0.68 |
| 3.5 STPY | 0.49 | 0.76 |
| 4.0 MSTPY | 0.31 | 0.44 |
| 1.1 STCO | 0.27 | 0.58 |
| 1.0 MSTCO | 0.23 | 0.18 |
| 1.3 D-MSTCO | 0.25 | 0.20 |
| 4.2 MSTLCB | 0.28 | 0.54 |

EXAMPLE 25

Dose-Dependent Loss of Eg5 from Mitotic Spindles

Figure 2:
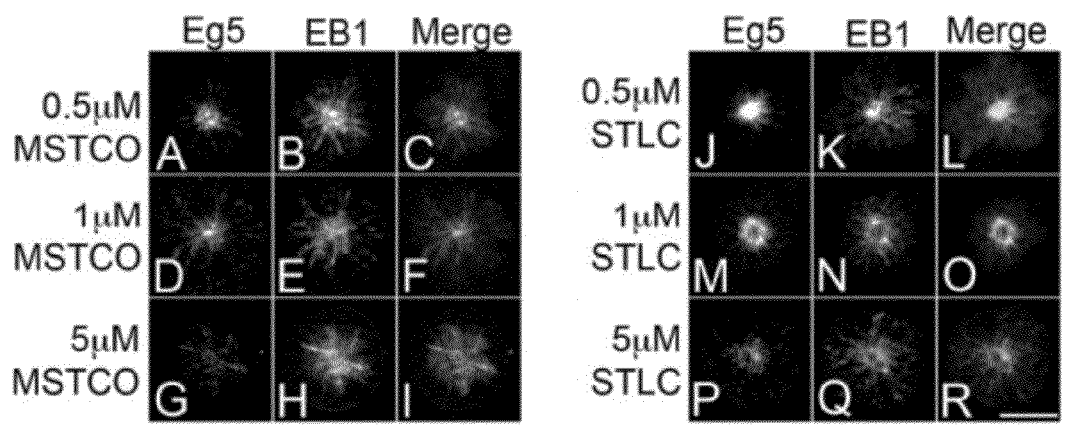
FIG. 2 illustrates HeLa cells incubated with increasing concentrations of either compound 1.0 (MSTCO) or compound 1.5 (STLC) and proved for the presence of Eg5 and EB1 (a probe for microtubules).

STLC, like monastrol and the other Eg5 inhibitors slows ADP release, thus slowing motor domain rebinding to the microtubule (Cochran and Gilbert, 2005; Skoufias et al., 2006; Lad et al., 2008). Referring now to FIG. 2, concentration-dependent loss of Eg5 from the spindle in compound 2.5 (STLC) and compound 1.0 (MSTCO) treated cells is illustrated. HeLa cells were incubated in increasing concentrations of either compound 1.0 (MSTCO) (Panels A-I) or compound 2.5 (STLC) (Panels J-R) for 4 hrs and then fixed and processed for Eg5 (red), the microtubule-associated protein EB1 (green) and DNA (blue). Eg5 was observed clustered at the center of the monopole (FIG. 2, Panels A and J), as previously reported (Kapoor et al., 2000). Additionally, imaging with equivalent exposure times over a range of inhibitor doses revealed that Eg5 was progressively lost from the spindle with increasing inhibitor, with Eg5 completely absent from the monopole in cells treated with 5 μM MSTCO (FIG. 2, Panel G). Thus, the behavior of Eg5 in the presence of compound 1.0 MSTCO was consistent with a mechanism of action whereby these allosteric modulators act by disrupting the ATPase cycle while allowing the motor to disengage from the microtubule track. Note that at equivalent concentrations, Eg5 localization to the monopolar spindle is consistently reduced in MSTCO-treated cells relative to STLC-treated cells. Bar, 10 μm.

The preceding examples can be repeated with similar success by substituting the generically or specifically described components and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A compound or its enantiomer, diastereomer, stereoisomer or its pharmaceutically acceptable salt, wherein said compound is one of the following:

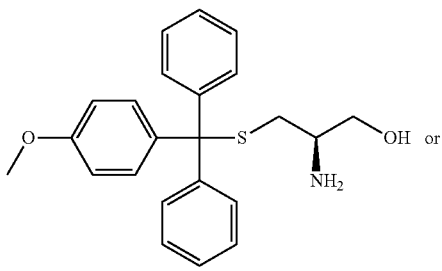

MSTCO 1.0
(R)-2-amino-3-(((4-methoxyphenyl)
diphenylmethyl)thio)propan-1-ol

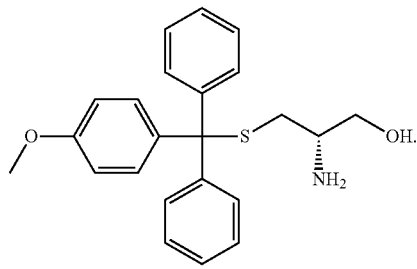

D-MSTCO 1.3
(S)-2-amino-3-(((4-methoxyphenyl)
diphenylmethyl)thio)propan-1-ol

2. A composition comprising a compound according to claim 1 and a therapeutic agent.

3. A composition which comprises a compound according to claim 1, or a pharmaceutically acceptable salt thereof, in association with a pharmaceutically acceptable diluent or carrier.

4. A process for preparing a compound according to claim 1 comprising:
reducing 2-amino-3-mercaptopropanoic acid;
using excess borane reagent in an organic solvent in an inert atmosphere;
quenching excess borane reagent with a second reagent; and
reacting with 4-methoxytrityl chloride.

5. The process of claim 4 wherein the second reagent comprises dimethylformamide.

6. A method of inhibiting activity of Eg5 or an Eg5 ortholog comprising providing a compound according to claim 1 to a cell.

7. The method of claim 6 further comprising measuring the activity of the Eg5 after contact with MSTCO or D-MSTCO.

8. The method of claim 6 wherein said inhibiting is of isolated Eg5.

9. A method of inhibiting chromosome movement comprising providing a compound according to claim 1 to a cell.

10. A method of inhibiting spindle pole separation comprising providing a compound according to claim 1 to a cell.

11. A method of inhibiting establishment of spindle bipolarity comprising providing a compound according to claim 1 to a cell.

12. A method of inhibiting mitosis of a dividing cell comprising providing a compound according to claim 1 to a cell.

13. The method of claim 12 further comprising measuring the rate of mitosis in the dividing cell after contacting the compound with the cell.

14. A method of treating leukemia, non-small cell lung cancer, colon cancer, melanoma, ovarian cancer and/or renal cancer in a patient in need thereof comprising:
administering to a patient in need thereof a pharmaceutically acceptable amount of a compound according to claim 1 or a salt with organic or inorganic acid to treat the leukemia, non-small cell lung cancer, colon cancer, melanoma, ovarian cancer and/or renal cancer.

15. The method of claim 14 further comprising monitoring the leukemia, non-small cell lung cancer, colon cancer, melanoma, ovarian and/or renal cancer in the patient after administration of a pharmaceutically acceptable amount of the compound.

16. The method of treating leukemia, non-small cell lung cancer, colon cancer, melanoma, ovarian and/or renal cancer of claim 14 wherein the compound is administered in a therapeutically effective dose by intravenous drug route or by oral route.

17. The method of claim 14 further comprising monitoring the patient for cancer progression.

* * * * *